US009617292B2

(12) United States Patent
Watanabe et al.

(10) Patent No.: US 9,617,292 B2
(45) Date of Patent: Apr. 11, 2017

(54) METHOD FOR PRODUCING NOVEL ORGANOMETALLIC COMPLEX AND AMINE COMPOUND

(71) Applicant: Kanto Kagaku Kabushiki Kaisha, Tokyo (JP)

(72) Inventors: Masahito Watanabe, Soka (JP); Toshihide Takemoto, Soka (JP); Kouichi Tanaka, Soka (JP); Kunihiko Murata, Soka (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/786,220

(22) PCT Filed: Apr. 22, 2014

(86) PCT No.: PCT/JP2014/061290
§ 371 (c)(1),
(2) Date: Oct. 22, 2015

(87) PCT Pub. No.: WO2014/175267
PCT Pub. Date: Oct. 30, 2014

(65) Prior Publication Data
US 2016/0060282 A1    Mar. 3, 2016

(30) Foreign Application Priority Data

Apr. 23, 2013 (JP) ................. 2013-090782

(51) Int. Cl.
| | | |
|---|---|---|
| C07F 17/02 | (2006.01) | |
| B01J 31/22 | (2006.01) | |
| C07C 255/58 | (2006.01) | |
| C07C 209/28 | (2006.01) | |
| C07F 15/00 | (2006.01) | |
| C07C 211/27 | (2006.01) | |
| C07C 211/29 | (2006.01) | |
| C07C 211/35 | (2006.01) | |
| C07C 211/40 | (2006.01) | |
| C07C 211/42 | (2006.01) | |
| C07C 213/02 | (2006.01) | |
| C07C 215/08 | (2006.01) | |
| C07C 217/60 | (2006.01) | |
| C07C 227/08 | (2006.01) | |
| C07C 227/32 | (2006.01) | |
| C07C 229/14 | (2006.01) | |
| C07C 253/30 | (2006.01) | |
| C07C 213/08 | (2006.01) | |
| C07D 217/14 | (2006.01) | |
| C07D 277/28 | (2006.01) | |
| C07D 209/48 | (2006.01) | |
| C07D 213/38 | (2006.01) | |
| C07D 213/42 | (2006.01) | |
| B01J 31/18 | (2006.01) | |
| C07B 43/04 | (2006.01) | |

(52) U.S. Cl.
CPC ............. *C07F 17/02* (2013.01); *B01J 31/183* (2013.01); *B01J 31/1815* (2013.01); *B01J 31/22* (2013.01); *B01J 31/2295* (2013.01); *C07B 43/04* (2013.01); *C07C 209/28* (2013.01); *C07C 211/27* (2013.01); *C07C 211/29* (2013.01); *C07C 211/35* (2013.01); *C07C 211/40* (2013.01); *C07C 211/42* (2013.01); *C07C 213/02* (2013.01); *C07C 213/08* (2013.01); *C07C 215/08* (2013.01); *C07C 217/60* (2013.01); *C07C 227/08* (2013.01); *C07C 227/32* (2013.01); *C07C 229/14* (2013.01); *C07C 253/30* (2013.01); *C07C 255/58* (2013.01); *C07D 209/48* (2013.01); *C07D 213/38* (2013.01); *C07D 213/42* (2013.01); *C07D 217/14* (2013.01); *C07D 277/28* (2013.01); *C07F 15/0033* (2013.01); *B01J 2231/64* (2013.01); *B01J 2531/822* (2013.01); *B01J 2531/827* (2013.01); *C07B 2200/07* (2013.01); *C07C 2101/14* (2013.01); *C07C 2102/08* (2013.01); *C07C 2102/10* (2013.01)

(58) Field of Classification Search
None
See application file for complete search history.

(56) References Cited

U.S. PATENT DOCUMENTS

| 2004/0267051 A1 | 12/2004 | Boerner et al. |
| 2010/0234596 A1 | 9/2010 | Watanabe et al. |

(Continued)

FOREIGN PATENT DOCUMENTS

| JP | 2004-256511 | 9/2004 |
| JP | 2004-537588 A | 12/2004 |

(Continued)

OTHER PUBLICATIONS

Abdel-Magid et al., Reductive Amination of Aldehydes and Ketones with Sodium Triacetoxyborohydride. Studies on Direct and Indirect Reductive Amination Procedures(1). J Org Chem. May 31, 2006;61(11):3849-3862.

(Continued)

*Primary Examiner* — Heidi Reese
(74) *Attorney, Agent, or Firm* — Wolf, Greenfield & Sacks, P.C.

(57) ABSTRACT

The purpose of the invention is to provide a novel organometallic compound that can be utilized as a catalyst having high generality, high activity, and excellent functional group selectivity. The invention pertains to a novel organometallic compound represented by general formula (1) that catalyzes a reductive amination reaction.

13 Claims, 7 Drawing Sheets

(56) References Cited

U.S. PATENT DOCUMENTS

| | | |
|---|---|---|
| 2012/0065426 A1 | 3/2012 | Watanabe et al. |
| 2013/0065864 A1 | 3/2013 | Habtemariam et al. |

FOREIGN PATENT DOCUMENTS

| | | |
|---|---|---|
| JP | 4059978 B2 | 3/2008 |
| JP | 2010-235604 A | 10/2010 |
| JP | 2012-62270 A | 3/2012 |
| WO | WO 2011/148124 A1 | 12/2011 |

OTHER PUBLICATIONS

Bomann et al., A Mild, Pyridine-Borane-Based Reductive Amination Protocol. J. Org. Chem. 1995;60(18):5995-5996.

Borch et al., the Cyanohydridoborate Anion as a Selective Reducing Agent. J. Am. Chem. Soc. 1971;93(12):2897-2904.

Burkhardt et al., Reductive amination with 5-ethyl-2-methylpyridine borane. Tetrahedron Lett. 2008;49(35):5152-5155.

Dickson et al., Anion Binding and Luminescent Sensing using Cationic Ruthenium(II) Aminopyridine Complexes. Chem Eur J. 2008;14:7296-7305.

Emerson et al., Secondary and tertiary amines from nitro compounds. JACS. Mar. 1941;63:749-751.

Gómez et al., Diastereospecific and diastereoselective syntheses of Ruthenium(II) complexes using N,N'bidentate ligands aryl-pyridin-2-ylmethyl-amine ArNH-CH2-2-C5H4N and their oxidation to imine ligands. Inorg Chem. Mar. 20, 2006;45(6):2483-93.

Gross et al., Synthesis of primary amines: first homogeneously catalyzed reductive amination with ammonia. Org Lett. Jun. 13, 2002;4(12):2055-8.

Johnson et al., N-Alkylation of amides. A novel procedure. J. Org. Chem. 1962. 27;2205.

Kitamura et al., Catalytic Leuckart-Wallach-type reductive amination of ketones. J Org Chem. Nov. 29, 2002;67(24):8685-7.

Nugent et al., Chiral Amine Synthesis—Recent Developments and Trends for Enamide Reduction, Reductive Amination, and Imine Reduction. Adv. Synth. Catal. 2010;352:753-819.

Tararov et al., On the reductive amination of aldehydes and ketones catalyzed by homogeneous Rh(I) complexes. Chem. Commun 2000;1867-1868.

[No Author Listed] Nomenclature of Coordination Complexes. Sep. 7, 2015. Chemistry LibreTexts™. Retrieved from http://chem.libretexts.org/Core/Inorganic_Chemistry/Coordination_Chemistry/Basics_of_Coordination_Chemistry/Nomenclature_of_Coordination_Complexes on Oct. 24, 2016.

Lei et al., Fast reductive amination by transfer hydrogenation "on water". Chem Eur J. Mar. 18, 2013;19(12):4021-9. doi:10.1002/chem.201204194.

Wang et al., A versatile catalyst for reductive amination by transfer hydrogenation. Angew Chem Int Ed Engl. Oct. 4, 2010;49(41):7548-52. doi: 10.1002/anie.201002944.

Reaction Example 1

Reaction Example 2

Reaction Example 3

Reaction Example 4

Reaction Example 5

Reaction Example 6

Reaction Example 7

Reaction Example 8

Reaction Example 9

Reaction Example 10

Reaction Example 11

Reaction Example 12

Reaction Example 13

Reaction Example 14

Reaction Example 1 5

Reaction Example 1 6

Reaction Example 1 7

Reaction Example 1 8

Reaction Example 1 9

| Reaction Example | Catalyst | AcOH (X eq) | yield (%) |
|---|---|---|---|
| 19 | 3 | 1 | 92 |
| 20 | 4 | 1 | 83 |
| 21 | 4 | 2 | 90 |
| 22 | 5 | 1 | 62 |
| 23 | 6 | 1 | 58 |
| 24 | 7 | 1 | 50 |

Reaction Example 2 5 — 2 9

S/C = 1000

| Reaction Example | Catalyst | yield (%) |
|---|---|---|
| 25 | 3 | 100 |
| 26 | 4 | 100 |
| 27 | 5 | 100 |
| 28 | 6 | 100 |
| 29 | 7 | 90 |

Reaction Example 3 0

S/C = 500

94% yield

Reaction Example 3 1

Reaction Example 3 2

Reaction Example 3 3

Reaction Example 3 4

Reaction Example 3 5

Reaction Example 3 6

Reaction Example 3 7

Reaction Example 38

Reaction Example 39

Reaction Example 40

US 9,617,292 B2

METHOD FOR PRODUCING NOVEL ORGANOMETALLIC COMPLEX AND AMINE COMPOUND

RELATED APPLICATION

This application is a national stage filing under 35 U.S.C. §371 of PCT International application PCT/JP2014/061290, filed Apr. 22, 2014.

TECHNICAL FIELD

The present invention relates to a novel organometallic complex. The present invention also relates to a catalyst of superior practical use comprising said organometallic complex. The present invention further relates to a use of said catalyst in reductive amination reaction.

BACKGROUND ART

Production method of amine compounds by the reaction of ammonia or a primary or secondary amine compound and a carbonyl compound is known as reductive amination reaction, which is one of the standard methods for producing amine compounds. As methods for producing amine compounds by reductive amination reaction known from the prior art, following methods are known: 1) a method by hydrogenation reaction using solid catalyst such as Raney Ni, Raney Co, Pt/activated carbon and Pd/activated carbon as heterogeneous catalyst, 2) a method using boron-based reactant such as $NaBH_3CN$ and $NaBH(OAc)_3$ as hydride reducing agent, and 3) a method using metal complex catalyst as homogeneous catalyst.

A method of 1) is described in, for example, J. Am. Chem. Soc. 1941, 63, 749 (Non-patent Document 1) and J. Org. Chem. 1962, 27, 2205 (Non-Patent Document 2).

As a method of 2), the following methods are known: a) a method using $NaBH_3CN$ described in J. Am. Chem. Soc. 1971, 93, 2897 (Non-Patent Document 3), b) a method using $NaBH(OAc)_3$ described in J. Org. Chem. 1996, 61, 3849 (non-patent document 4), c) a method using pyridine borane described in J. Org. Chem. 1995, 60, 5995 (Non-Patent Document 5), d) a method using 2-picoline borane described in JP A 2004-256511 (Patent Document 1), and e) a method using 5-ethyl-2-methylpyridine borane described in Tetrahedron Letters 2008, 49, 5152-5155 (non-Patent Document 6).

As a method of 3), the following methods are known: a production method to obtain primary amines by reacting carbonyl compound, ammonia, and hydrogen under the presence of hydrogenation catalyst, described in JP No. 4059978 (Patent Document 2); a method by hydrogenation reaction using rhodium complex having phosphine ligand, described in Chem. Comm., 2000, 1867-1868 (Non-Patent Document 7); a method by hydrogenation reaction using a combination of $[Rh(cod)Cl_2]_2$ complex and TPPTS ligand described in Org. Lett. 2002, 4, 2055-2058 (Non-Patent Document 8); a method using $[Cp^*RhCl_2]_2$ as complex catalyst, ammonium formate as amine source and hydrogen source, described in J. Org. Chem. 2002, 67 8685-8687 (Non-Patent Document 9); and a method by reductive hydride-transfer amination of carbonyl compound and amine compound under the presence of hydrogen donor as reducing agent and transition metal complex catalyst containing at least one metal selected from the group consisting of Ru, Rh and Ir, described in JP A 2004-537588 (Patent Document 3).

However, production methods by hydrogenation reaction using solid catalyst have a problem in terms of safety and reaction operability because the methods require a pressure-resistant reactor for hydrogen gas used as hydrogen source, and a problem of not applicable to substrates having carbon-carbon multiple binding sites and hydrogenation-susceptible functional groups such as cyano group and nitro group. Since boron-based reactants do not require a pressure-resistant reactor, the methods using them are superior in operability; however, they are inferior in terms of economic and environmental aspects because the reaction is not a catalytic reaction, and the following problems also exist in each reactant.

Regarding the method using $NaBH_3CN$, industrial use is difficult because of its toxicity. In the method using $NaBH(OAc)_3$, there is a restriction of solvent to be used due to its solubility, and the use of an excess amount is required because $NaBH(OAc)_3$ has only one hydride source in the molecule. Regarding the method using pyridine borane, there are problems that the storage stability of the reagent itself is poor, and the reagent decomposes at 54° C. or higher. In the method using 2-picoline borane, although the stability of the reactant 2-picoline borane is higher than that of pyridine borane, it has a handling problem because its melting point is 44-45° C. 5-Ethyl-2-methylpyridine borane has a problem, similar to the above two pyridine-borane-based reactants, that the removal of the reactant from reaction solution is not easy.

As an example of using a homogeneous catalyst, in the method described in JP No. 4059978, a pressure-resistant reactor is required because hydrogen is used as a hydrogen source, and its industrial implementation is problematic from the standpoint of safety and reaction operability because reaction is carried out at high temperature (150° C.) and high pressure (50 atm or more) conditions. The method described in Chem. Comm., 2000, 1867-1868 is a reaction under high pressure (50 atm), and alcohol by-products are produced and the selectivity of amine is poor, so that the method will not be an efficient production method of amine compounds. The hydrogenation reaction by combination of $[Rh(cod)Cl]_2$ complex and TPPTS ligand, described in J. Org. Lett. 2002, 4, 2055-2058, is performed at high temperature and high pressure conditions, so that its industrial implementation is problematic from the standpoint of safety and reaction operability.

As shown in J. Org. Chem. 2002, 67, 8685-8687, in the method using a $[Cp^*RhCl_2]_2$ complex, i.e., organometallic complex, as an catalyst, solid ammonium formate is used as a hydrogen source and an amine source; therefore it is an excellent method in terms of reaction operability and safety, whereas its industrial use is problematic because catalytic activity is low. The method described in JP A 2004-537588 exhibits very poor reaction efficiency, i.e., a ratio of [substrate/catalyst] of approximately 50-100, and in some cases alcohol by-products are generated and reaction does not complete; thus, its industrial implementation is difficult.

A method for obtaining optically active amine by diastereoselective reductive amination reaction using optically active amine as an amine source is also known. In Adv. Synth. Catal. 2010, 352, 753-819 (Non-Patent Document 10), the following method is described: optically active α-methylbenzylamine is used as an amine source, and under the co-presence of Lewis acid such as Ti(O-i-Pr)$_4$ and Yb(OAc)$_3$, using a solid catalyst such as Raney Ni, Pd/C or Pt/C, a highly diastereoselective reductive amination reaction is carried out under hydrogenation conditions to obtain optically active amine by the deprotection of protecting groups. In addition, in the same document a method of diastereoselective reductive amination reaction, using optically active tert-butyl sulfinamide as the amine source, under the presence of Ti(OEt)$_4$ and using DIBAL at a reaction temperature of −48° C. or using L-selectride, is described.

However, since the former method requires an equimolar or more of Lewis acid relative to the substrate, and the amount of solid catalyst used is large; therefore, the production cost is high, and post-treatment after the reaction is complicated; thus, its industrial implementation is problematic from the viewpoint of reaction operability and safety. In the latter reaction, under cryogenic conditions of −48° C., 2 equivalents of Lewis acid relative to the substrate and expensive amine are required; therefore, from the viewpoint of reaction operability, safety and economical aspect, the method cannot be a practical production method similar to the former method.

In JP A 2010-235604 (Patent Document 4) and JP A 2012-062270 (Patent Document 5), a reductive amination reaction using formic acid or ammonium formate as a hydrogen source is described.

PRIOR ART DOCUMENTS

Patent Documents

[Patent Document 1] JP A 2004-256511
[Patent Document 2] JP No. 4059978
[Patent Document 3] JP A 2004-537588
[Patent Document 4] JP A 2010-235604
[Patent Document 5] JP A 2012-062270

Non-Patent Documents

[Non-Patent Document 1] J. Am. Chem. Soc. 1941, 63, 749.
[Non-Patent Document 2] J. Org. Chem. 1962, 27, 2205.
[Non-Patent Document 3] J. Am. Chem. Soc. 1971, 93, 2897.
[Non-Patent Document 4] J. Org. Chem. 1996, 61, 3849.
[Non-Patent Document 5] J. Org. Chem. 1995, 60, 5995.
[Non-Patent Document 6] Tetrahedron Letters 2008, 49, 5152-5155.
[Non-Patent Document 7] Chem. Comm., 2000, 1867-1868.
[Non-Patent Document 8] Org. Lett. 2002, 4, 2055-2058.
[Non-Patent Document 9] J. Org. Chem. 2002, 67, 8685-8687.
[Non-Patent Document 10] Adv. Synth. Catal. 2010, 352, 753-819.

SUMMARY OF THE INVENTION

Problems to be Solved by the Invention

An object of the present invention is to provide a novel production method of amine compounds using a highly versatile novel catalyst with high activity and superior functional group selectivity, for the production of amine compounds by reductive amination reaction. A further object of the present invention is to provide a novel production method of amine compounds, using inexpensive optically active amine as the amine source, and using a novel catalyst that enables highly diastereoselective reductive amination reaction that can be carried out with inexpensive reducing agents and in a small amount of catalyst.

Means for Solving the Problems

The present inventors have encountered a new problem during carrying out research on the production method of amine compounds by reductive amination reaction of carbonyl compounds and amine compounds; that is, in the production method described in Patent Document 4, when carrying out the reductive amination reaction using an optically active amine as the amine source, it is unclear that if the reaction proceeds in a highly diastereoselective manner, and whether optically active amines can be obtained with high efficiency. In continuing intensive research to solve the above problems, the present inventors have found that highly diastereoselective reductive amination reaction is possible by using ruthenium, rhodium and iridium complexes having nitrogen-containing ligands with a specific structure, and that optically active amine with high optical purity can be obtained. As a result of further investigation, the present inventors have completed the present invention Namely, the present invention relates to the following.

[1] An organometallic compound of the following general formula (1):

[Formula 1]

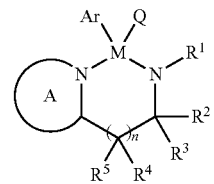

(1)

wherein

Ar is an aromatic compound or a cyclopentadienyl group, in which one or more hydrogen atoms may be substituted by a substituent W, the substituent W is a saturated or unsaturated C1-C20 hydrocarbon group, a 6- to 20-membered aryl group in which a carbon atom may be replaced by a heteroatom, a 3- to 20-membered heterocyclyl group, a C1-C20 alkoxy group, —C(=O)—R$^a$, —C(=O)—OR$^a$, a hydroxyl group, —NR$^a$R$^b$, —C(=O)—NR$^a$R$^b$, a nitro group, a cyano group, —PR$^a$R$^b$, a C1-C20 sulfenyl group, a sulfo group, a mercapto group, —SiR$^a$R$^b$R$^c$, a halogen group or —S(=O)$_1$—R$^a$, Q is a hydride group or an anionic group, M is ruthenium, rhodium or iridium, R$^1$ is an electron withdrawing group, R$^2$, R$^3$, R$^4$ and R$^5$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a C1-C20 alkoxy group, —C(=O)—OR$^a$, a C1-C20 fluoroalkyl group, —C(=O)—R$^a$, —S(=O)$_2$—R$^a$, a hydroxyl group, —NR$^a$R$^b$, —C(=O)—NR$^a$R$^b$, a C1-C20 sulfenyl group, or —SiR$^a$R$^b$R$^c$, wherein one or more hydrogen atoms of these groups may be substituted by the substituent W,
R$^a$, R$^b$ and R$^c$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom,
R$^2$ and R$^3$ and/or R$^4$ and R$^5$ may be bonded to each other to form a ring,
one of R$^2$ and R$^3$, and one of R$^4$ or R$^5$ may be bonded to each other to form a ring,
R$^1$ and R$^2$, or R$^1$ and R$^3$ may be bonded to each other to form a ring, the carbon atom to which R$^2$ and R$^3$ are bonded, and/or the carbon atom to which R$^4$ and R$^5$ are bonded is/are asymmetric carbon atoms,
n is an integer of 0 or 1,
A is a saturated or unsaturated heterocycle containing at least one nitrogen atom, wherein one or more hydrogen atoms may be substituted by a substituent W.
[2] The organometallic compound according to [1], wherein the electron-withdrawing group is —S(=O)$_2$—R$^a$, a 6- to 20-membered aryl group in which a carbon atom may be replaced by a heteroatom, —C(=O)—OR$^a$, —C(=O)—R$^a$, —C(=O)—NR$^a$R$^b$, —C(=S)—NR$^a$R$^b$, a C1-C20 sulfenyl group or a perfluoroalkyl group, in which one or more hydrogen atoms of these groups may be substituted by a substituent W.
[3] The organometallic compound according to [1] or [2], wherein the electron-withdrawing group is —S(=O)$_2$—R$^a$, —C(=O)—R$^a$, or —C(=O)—NR$^a$R$^b$, in which one or more hydrogen atoms of these groups may be substituted by a substituent W.
[4] The organometallic compound according to any one of [1] to [3], characterized in that Ar is a cyclopentadienyl group in which one or more hydrogen atoms may be substituted by a substituent W, and M is iridium or rhodium.
[5] The organometallic compound according to any one of [1] to [4], characterized in that n=0.
[6] The organometallic compound according to any one of [1] to [5], wherein A is a saturated or unsaturated 4- to 6-membered heterocycle having only one nitrogen atom as the ring member heteroatom.
[7] The organometallic compound according to any one of [1] to [5], wherein A is a saturated or unsaturated 4- to 6-membered heterocycle comprising one or more heteroatoms selected from the group consisting of nitrogen atom, oxygen atom and sulfur atom, in addition to one nitrogen atom.
[8] The organometallic compound according to any one of [1] to [7], wherein A is an aromatic ring.
[9] The organometallic compound according to any one of [1] to [8], wherein an organometallic complex of general formula (1) is an optically active substance.
[10] A catalyst used for a reducing reaction or a hydrogenation reaction of one or more kinds selected from the group consisting of imine, iminium cation and enamine, or a reducing reaction or a hydrogenation reaction of one or more kinds selected from the group consisting of imine, iminium cation and enamine that are generated in a system of mixing a carbonyl compound and an amine compound, wherein the catalyst comprises at least one organometallic compound according to any one of [1] to [9].

[11] A method for producing an amine compound, characterized in that the amine compound is produced, under the presence of the organometallic compound according to any one of [1] to [9], using a hydrogen-donating organic compound or inorganic compound or hydrogen as the hydrogen source, by the reduction or hydrogenation of one or more compounds selected from the group consisting of a compound of general formula (2):

[Formula 2]

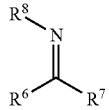

(2)

wherein
R$^6$ and R$^7$ are, independently of one another, a hydrogen atom, a hydrocarbyl group, an aryl group in which a carbon atom may be replaced by a heteroatom, a 6- to 20-membered alkylaryl group in which a carbon atom of the aryl may be replaced by a heteroatom, a 6- to 20-membered aralkyl group in which a carbon atom of the aryl may be replaced by a heteroatom, a heterocyclyl group, a carboxyl group, an ester group or an acyl group, wherein one or more hydrogen atoms of these groups may be substituted by a substituent W,
R$^8$ is a hydrogen atom, a hydroxyl group, a hydrocarbyl group, an aryl group in which a carbon atom may be replaced by a heteroatom, a 6- to 20-membered alkylaryl group in which a carbon atom of the aryl may be replaced by a heteroatom, a 6- to 20-membered aralkyl group in which a carbon atom of the aryl may be replaced by a heteroatom, a heterocyclyl group, a sulfonyl group in which a carbon atom may be replaced by a heteroatom, an alkoxy group, an acyl group, an ester group, a carboxyl group, a phosphinyl group, a sulfinyl group or a silyl group, wherein one or more hydrogen atoms of these groups may be substituted by a substituent W, R$^6$ and R$^7$, or R$^6$ and R$^8$ may be bonded to each other to form a ring; a cation of general formula (3):

[Formula 3]

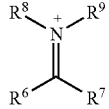

(3)

wherein
R$^6$ and R$^7$ represent the same meanings as defined above,
R$^8$ and R$^9$ are, independently of one another, a hydrogen atom, a hydroxyl group, a hydrocarbyl group, an aryl group in which a carbon atom may be replaced by a heteroatom, a 6- to 20-membered alkylaryl group in which a carbon atom of the aryl may be replaced by a heteroatom, a 6- to 20-membered aralkyl group in which a carbon atom of the aryl may be replaced by a heteroatom, a heterocyclyl group, a sulfonyl group in which a carbon atom may be replaced by a heteroatom, an alkoxy group, an acyl group, an ester group, a carboxyl group, a phosphinyl group, a sulfinyl group or a silyl group, wherein one or more hydrogen atoms of these groups may be substituted by a substituent W, one or more selected from $R^6$ and $R^7$, $R^6$ and $R^8$, $R^7$ and $R^9$, and $R^8$ and $R^9$, may be bonded to each other to form a ring; and a compound of general formula (4):

[Formula 4]

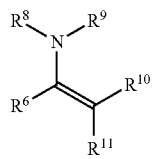

(4)

wherein $R^6$, $R^8$, and $R^9$ have the same meanings as defined above, $R^{10}$ and $R^{11}$ are, independently of one another, a hydrogen atom, a hydrocarbyl group, an aryl group in which a carbon atom may be replaced by a heteroatom, a heterocyclyl group, a carboxyl group, an ester group, or an acyl group, wherein one or more hydrogen atoms of these groups may be substituted by a substituent W, one or more selected from $R^6$ and $R^8$, $R^6$ and $R^{11}$, $R^8$ and $R^9$, $R^9$ and $R^{10}$, and $R^{10}$ and $R^{11}$, may be bonded to each other to form a ring; or one or more compounds selected from the group consisting of a compound of general formula (2), a cation of general formula (3), and a compound of general formula (4), which are generated by mixing a carbonyl compound and an amine compound in a system.

[12] A method for producing an amine compound, characterized in that the amine compound is produced, using a hydrogen-donating organic compound or inorganic compound or hydrogen as the hydrogen source, under the presence of an organometallic compound of general formula (5):

[Formula 5]

$(ArMQ_2)_p$ (5)

wherein

Ar is an aromatic compound or a cyclopentadienyl group, in which one or more hydrogen atoms may be substituted by a substituent W, the substituent W is a saturated or unsaturated C1-C20 hydrocarbon group, a 6- to 20-membered aryl group in which a carbon atom may be replaced by a heteroatom, a 3- to 20-membered heterocyclyl group, a C1-C20 alkoxy group, —C(=O)—$R^a$, —C(=O)—$OR^a$, a hydroxyl group, —$NR^aR^b$, —C(=O)—$NR^aR^b$, a nitro group, a cyano group, —$PR^aR^b$, a C1-C20 sulfenyl group, a sulfo group, a mercapto group, —$SiR^aR^bR^c$, a halogen group or —S(=O)$_2$—$R^a$, Q is a hydride group or an anionic group, M is ruthenium, rhodium or iridium, p represents an integer of 2 or greater; and an organic compound of general formula (6):

[Formula 6]

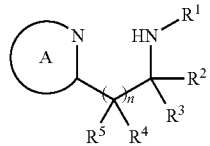

(6)

wherein $R^1$ is an electron withdrawing group, $R^2$, $R^3$, $R^4$ and $R^5$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a C1-C20 alkoxy group, —C(=O)—$OR^a$, a C1-C20 fluoroalkyl group, —C(=O)—$R^a$, —S(=O)$_2$—$R^a$, a hydroxyl group, —$NR^aR^b$, —C(=O)—$NR^aR^b$, a C1-C20 sulfenyl group, or —$SiR^aR^bR^c$, wherein one or more hydrogen atoms of these groups may be substituted by a substituent W, $R^a$, $R^b$ and $R^c$ are, independently of one another, a hydrogen atom, a saturated or unsaturated C1-C20 alkyl group, a saturated or unsaturated C3-C20 cycloalkyl group or a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom, $R^2$ and $R^3$ and/or $R^4$ and $R^5$ may be bonded to each other to form a ring, one of $R^2$ and $R^3$, and one of $R^4$ or $R^5$ may be bonded to each other to form a ring, $R^1$ and $R^2$, or $R^1$ and $R^3$ may be bonded to each other to form a ring, the carbon atom to which $R^2$ and $R^3$ are bonded, and/or the carbon atom to which $R^4$ and $R^5$ are bonded is/are asymmetric carbon atoms, n is an integer of 0 or 1, A is a saturated or unsaturated heterocycle containing at least one nitrogen atom, wherein one or more hydrogen atoms may be substituted by a substituent W;

by the reduction or hydrogenation of one or more compounds selected from the group consisting of a compound of general formula (2):

[Formula 7]

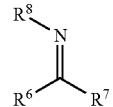

(2)

wherein $R^6$ and $R^7$ are, independently of one another, a hydrogen atom, a hydroxyl group, a hydrocarbyl group, an aryl group in which a carbon atom may be replaced by a heteroatom, a 3- to 20-membered alkylaryl group in which a carbon atom of the aryl may be replaced by a heteroatom, a 3- to 20-membered aralkyl group in which a carbon atom of the aryl may be replaced by a heteroatom, a heterocyclyl group, a carboxyl group, an ester group or an acyl group, wherein one or more hydrogen atoms of these groups may be substituted by the substituent W, $R^8$ is a hydrogen atom, a hydroxyl group, a hydrocarbyl group, an aryl group in which a carbon atom may be replaced by a heteroatom, a 3- to 20-membered alkylaryl group in which a carbon atom of the aryl may be replaced by a heteroatom, a 3- to 20-membered aralkyl group in which a carbon atom of the aryl may be replaced by a heteroatom, a heterocyclyl group, a sulfonyl group in which a carbon atom may be replaced by a heteroatom, an alkoxy group, an acyl group, an ester group, a carboxyl group, a phosphinyl group, a sulfinyl group or a silyl group, wherein one or more hydrogen atoms of these groups may be substituted by a substituent W, $R^6$ and $R^7$, or $R^6$ and $R^8$ may be bonded to each other to form a ring; a cation of general formula (3):

[Formula 8]

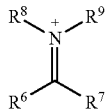

(3)

wherein
$R^6$ and $R^7$ represent the same meanings as defined above,
$R^8$ and $R^9$ are, independently of one another, a hydrogen atom, a hydroxyl group, a hydrocarbyl group, an aryl group in which a carbon atom may be replaced by a heteroatom, a heterocyclyl group, a sulfonyl group in which a carbon atom may be replaced by a heteroatom, an alkoxy group, an acyl group, an ester group, a carboxyl group, a phosphinyl group, a sulfinyl group or a silyl group, wherein one or more hydrogen atoms of these groups may be substituted by a substituent W,
one or more selected from $R^6$ and $R^7$, $R^6$ and $R^8$, $R^7$ and $R^9$, and $R^8$ and $R^9$, may be bonded to each other to form a ring; and
a compound of general formula (4):

[Formula 9]

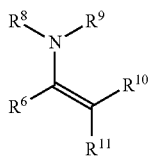

(4)

wherein
$R^6$, $R^7$, and $R^9$ have the same meanings as defined above,
$R^{10}$ and $R^{11}$ are, independently of one another, a hydrogen atom, a hydroxyl group, a hydrocarbyl group, an aryl group in which a carbon atom may be replaced by a heteroatom, a 3- to 20-membered alkylaryl group in which a carbon atom of the aryl may be replaced by a heteroatom, a 3- to 20-membered aralkyl group in which a carbon atom of the aryl may be replaced by a heteroatom, a heterocyclyl group, a carboxyl group, an ester group, or an acyl group, wherein one or more hydrogen atoms of these groups may be substituted by the substituent W,
one or more selected from $R^6$ and $R^8$, $R^6$ and $R^{11}$, $R^8$ and $R^9$, $R^9$ and $R^{10}$, and $R^{10}$ and $R^{11}$, may be bonded to each other to form a ring; or
one or more compounds selected from the group consisting of a compound of general formula (2), a cation of general formula (3), and a compound of general formula (4), which are generated by mixing a carbonyl compound and an amine compound in a system.

[13] The method for producing an amine compound according to [12], characterized in that in the organometallic compound of general formula (5), Ar is a cyclopentadienyl group which may have a substituent, and M is rhodium or iridium.

[14] The method for producing an amine compound according to any one of [11] to [13], wherein the carbonyl compound is a compound of general formula (7):

[Formula 10]

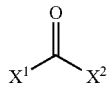

(7)

wherein
$X^1$ and $X^2$ are, independently of one another, a hydrogen atom, a hydroxyl group, a hydrocarbyl group, an aryl group in which a carbon atom may be replaced by a heteroatom, an alkylaryl group in which a carbon atom of the aryl may be replaced by a heteroatom, an aralkyl group in which a carbon atom of the aryl may be replaced by a heteroatom, a heterocyclyl group, a carboxyl group, an ester group, or an acyl group, wherein one or more hydrogen atoms of these groups may be substituted by a substituent W,
the substituent W is a saturated or unsaturated C1-C20 hydrocarbon group, a 6- to 20-membered aryl group in which a carbon atom may be replaced by a heteroatom, a 3- to 20-membered heterocyclyl group, a C1-C20 alkoxy group, —C(=O)—$R^a$, —C(=O)—$OR^a$, a hydroxyl group, —$NR^aR^b$, —C(=O)—$NR^aR^b$, a nitro group, a cyano group, —$PR^aR^b$, a C1-C20 sulfenyl group, a sulfo group, a mercapto group, —$SiR^aR^bR^c$, a halogen group or —S(=O)$_2$—$R^a$,
$R^a$, $R^b$ and $R^c$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom,
$X^1$ and $X^2$ may be bonded to each other to form a ring; and the amine compound to be mixed with the carbonyl compound in a system is an amine of general formula (8) or a salt thereof:

[Formula 11]

$NHY^1Y^2$  (8)

wherein
$Y^1$ and $Y^2$ are, independently of one another, a hydrogen atom, a hydroxyl group, a hydrocarbyl group, an aryl group in which a carbon atom may be replaced by a heteroatom, a 6- to 20-membered aralkyl group in which a carbon atom of the aryl may be replaced by a heteroatom, a 6- to 20-membered alkylaryl group in which a carbon atom of the aryl may be replaced by a heteroatom, a heterocyclyl group, a sulfonyl group in which a carbon atom may be replaced by a heteroatom, an alkoxy group, an acyl group, an ester group, a carboxyl group, a phosphinyl group, a sulfinyl group or a silyl group, wherein one or more hydrogen atoms of these groups may be substituted by the substituent W,
$Y^1$ and $Y^2$ may be bonded to each other to form a ring.

[15] The method for producing an amine compound according to any one of [11] to [14], characterized in that one or more compounds selected from the group consisting of a compound of general formula (2), a cation of general formula (3) and a compound of general formula (4) are optically active compounds.

[16] The method for producing an amine compound according to any one of [11] to [14], characterized in that one or more compounds selected from the group consisting of a compound of general formula (2), a cation of general formula (3) and a compound of general formula (4) are optically active compounds generated by the reaction of an optically active amine and a carbonyl compound.

[17] The method for producing an amine compound according to any one of [11] to [16], wherein the hydrogen-donating organic or inorganic compound is formic acid or formate.

Advantageous Effects of the Invention

The present invention enables to provide a novel catalyst with high versatility, high activity and superior functional group selectivity, as well as a highly-diastereoselective production method of amine compounds by reductive amination reaction of carbonyl compounds and amine compounds, using said catalyst. Furthermore, the invention enables to provide a highly diastereoselective and highly efficient production method of optically active amine using optically active amine as the amine source.

A metal complex catalyst of the present invention is extremely useful in reductive amination reaction under acidic conditions, which has been difficult to carry out with conventional metal complex catalysts. Reductive amination reaction is generally carried out under acidic conditions; however, many of conventional organometallic complex catalysts show high catalytic activity under neutral to basic conditions, and there are only a few of them showing high catalytic activity under acidic conditions at present. This is considered to be because, under acidic conditions, ligand is detached due to protonation, etc. and the complex is decomposed. Using the catalyst of the present invention, decomposition of the complex by detachment of ligand under acidic conditions can be suppressed by an electron withdrawing group, i.e., the substituent $R^1$, and as a result, high catalytic activity and diastereoselectivity can be considered to be achieved.

MODES FOR CARRYING OUT THE INVENTION

Figure 1:
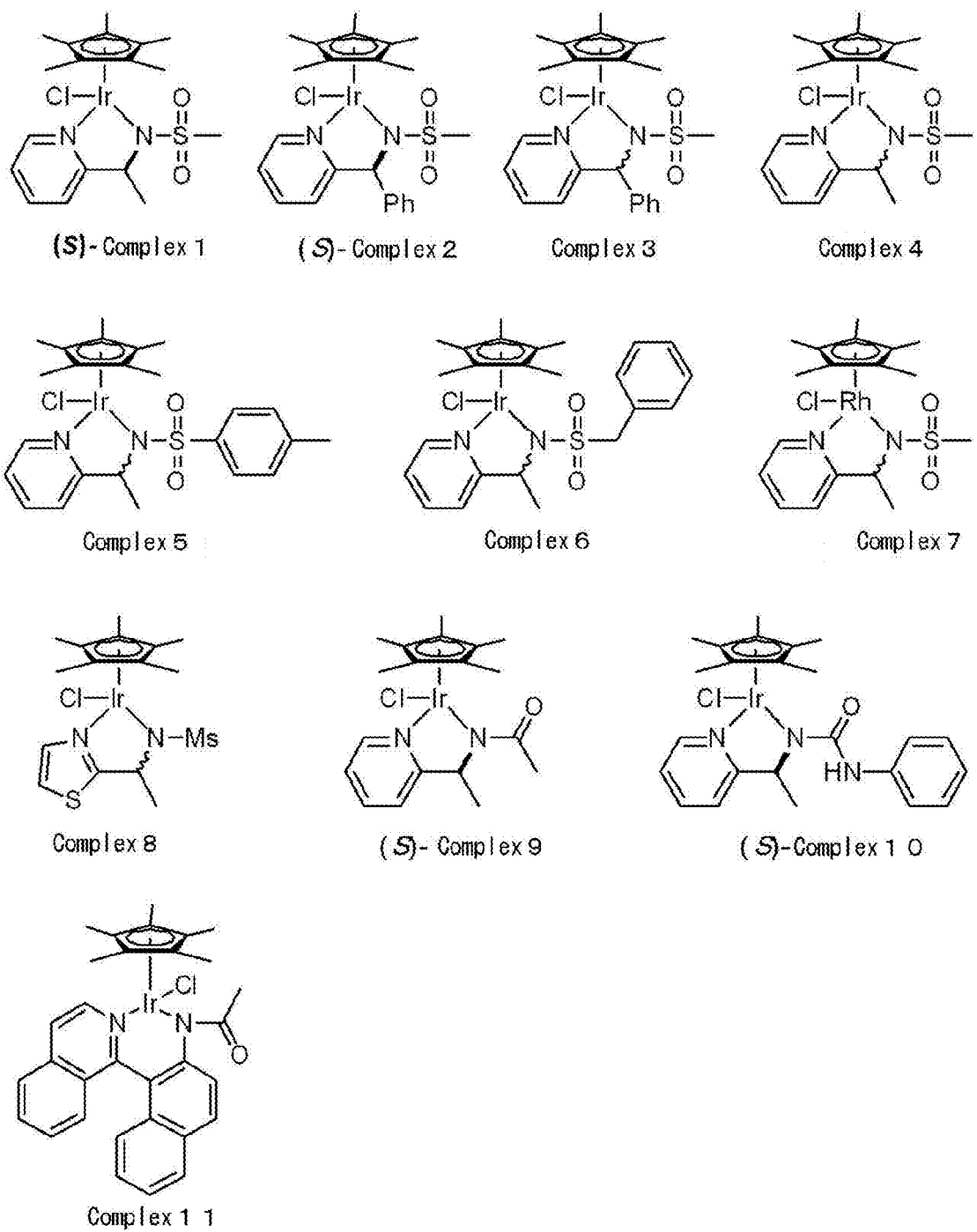
FIG. 1 shows organometallic complexes used in the Reaction Examples.
Figure 2:
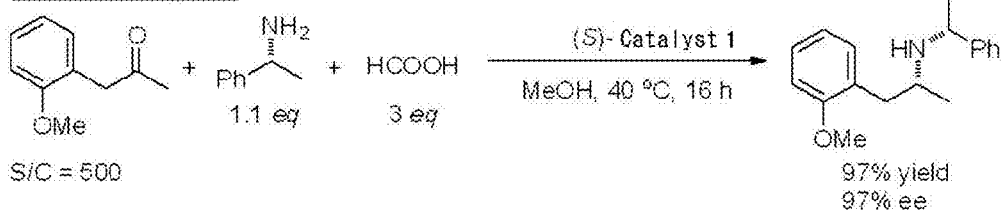
FIG. 2 shows reaction formulae of Reaction Examples 1 to 6.
Figure 2:
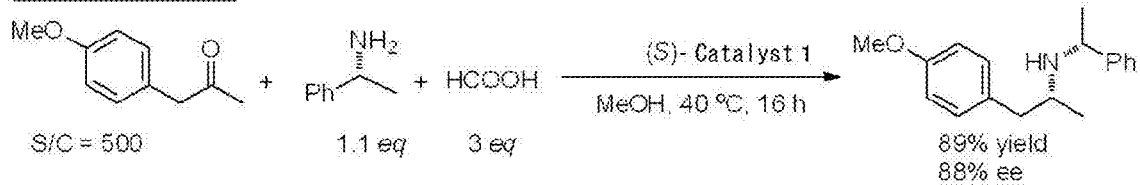
Figure 2:
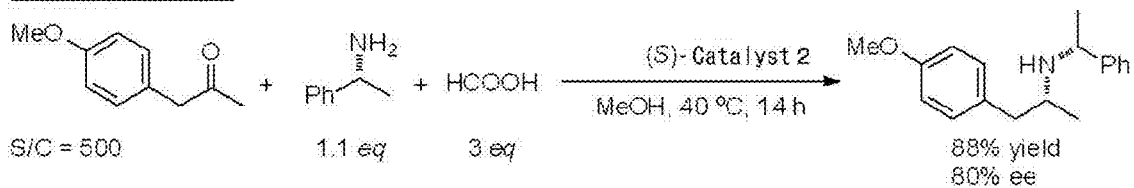
Figure 2:
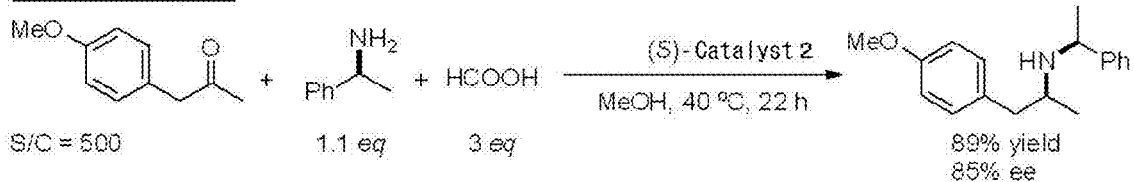
Figure 2:
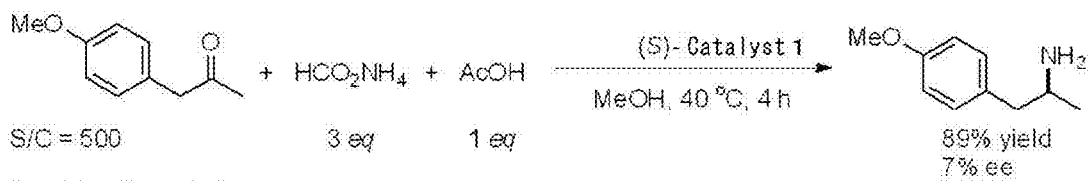
Figure 2:
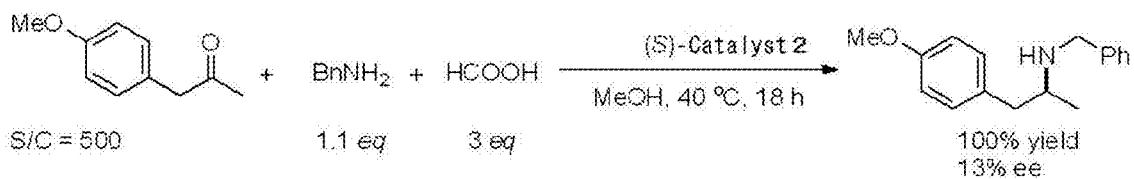
Figure 3:
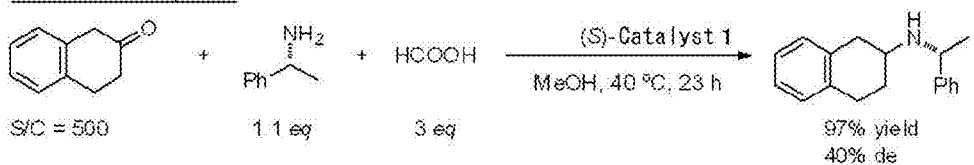
FIG. 3 shows reaction formulae of Reaction Examples 7 to 14.
Figure 3:
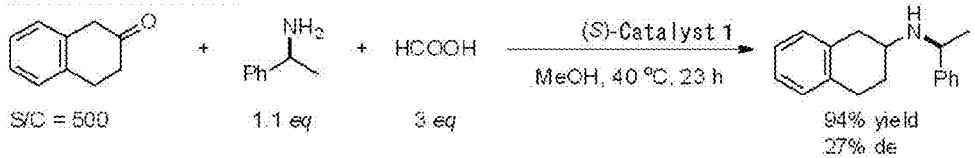
Figure 3:
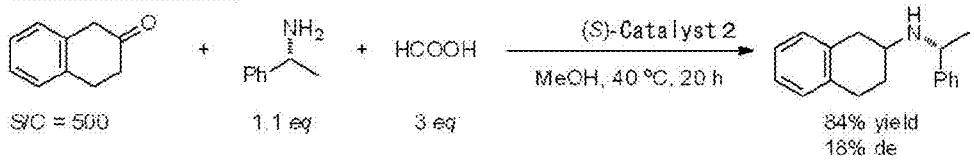
Figure 3:
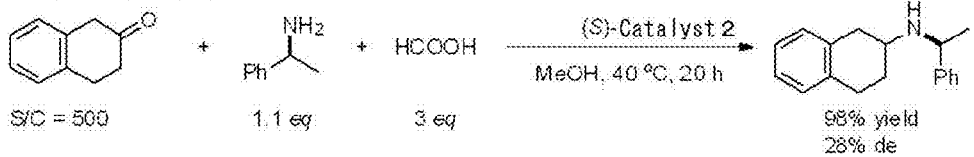
Figure 3:
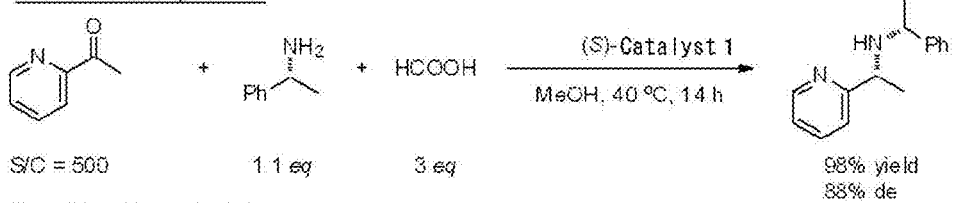
Figure 3:
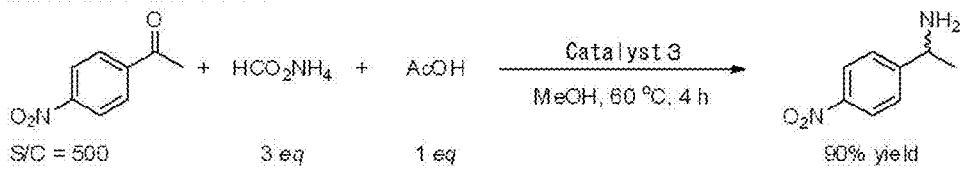
Figure 3:
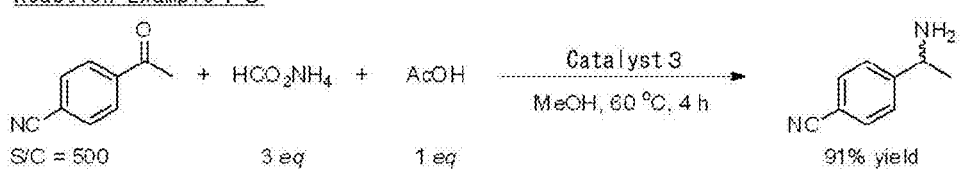
Figure 3:
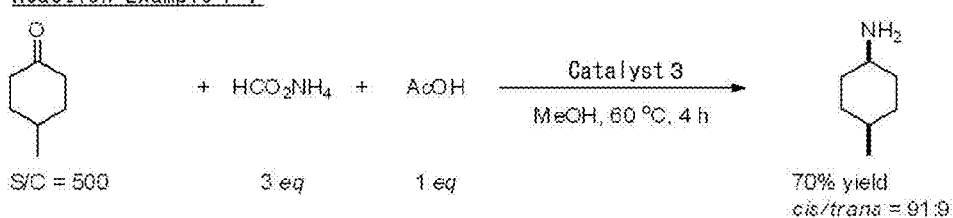
Figure 4:
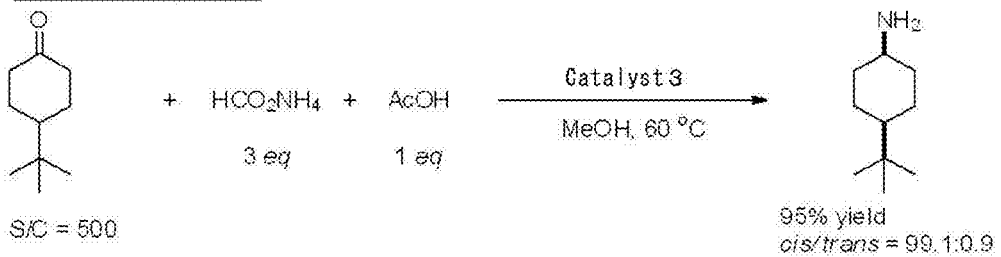
FIG. 4 shows reaction formulae of Reaction Examples 15 to 24.
Figure 4:
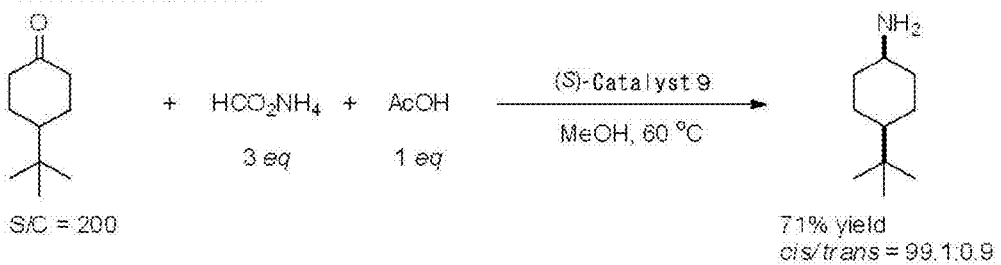
Figure 4:
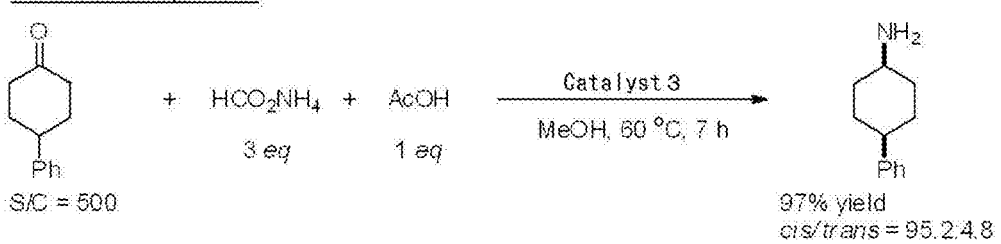
Figure 4:
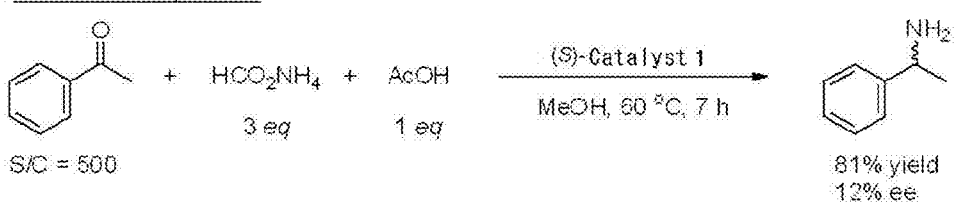
Figure 4:
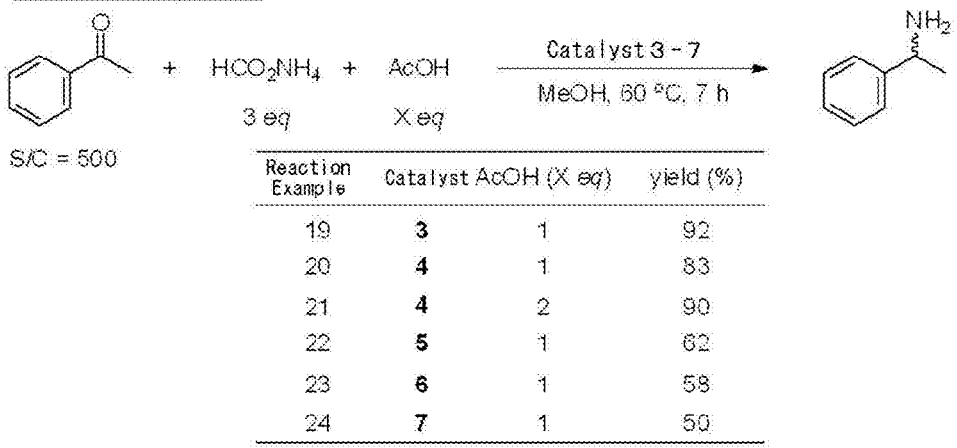
Figure 5:
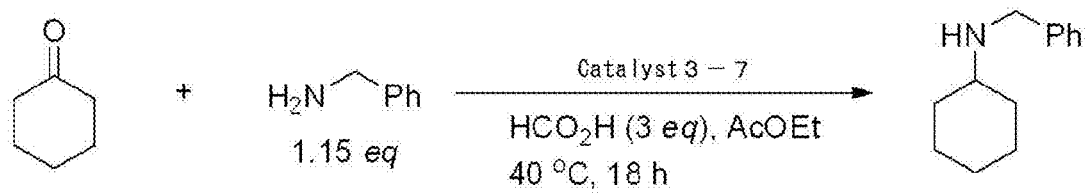
FIG. 5 shows reaction formulae of Reaction Examples 25 to 30.
Figure 5:
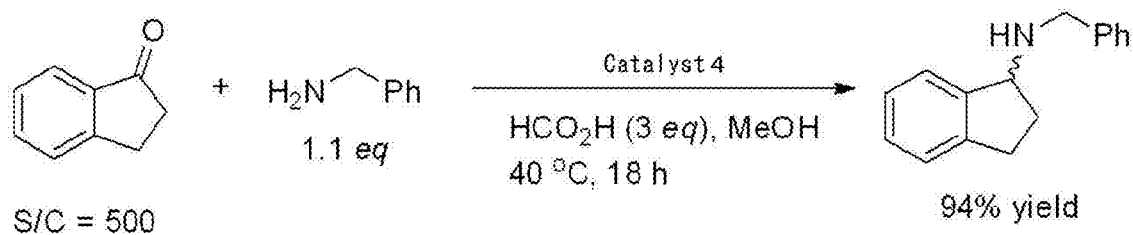
Figure 6:
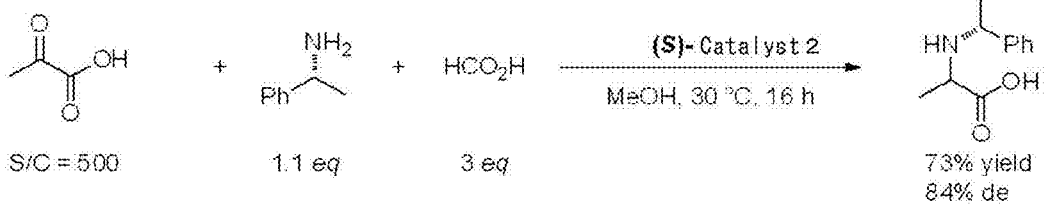
FIG. 6 shows reaction formulae of Reaction Examples 31 to 37.
Figure 6:
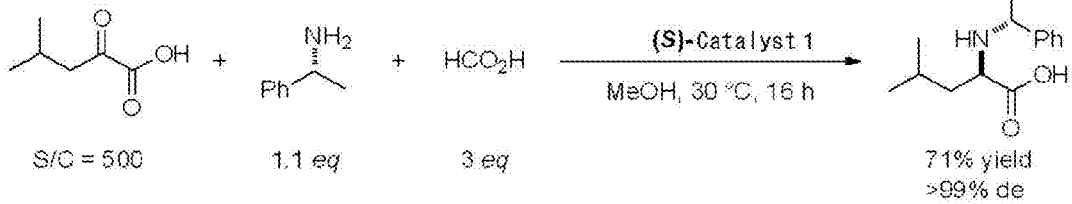
Figure 6:
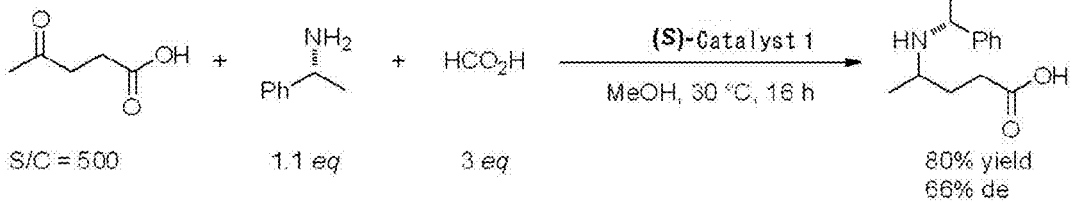
Figure 6:
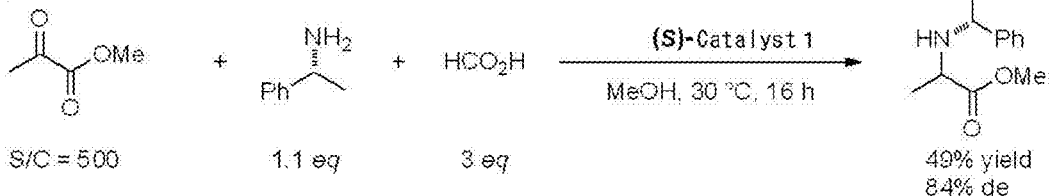
Figure 6:
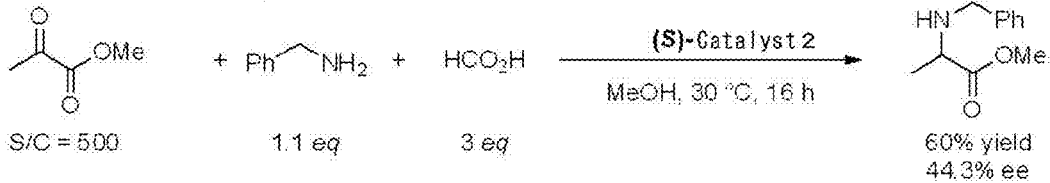
Figure 6:
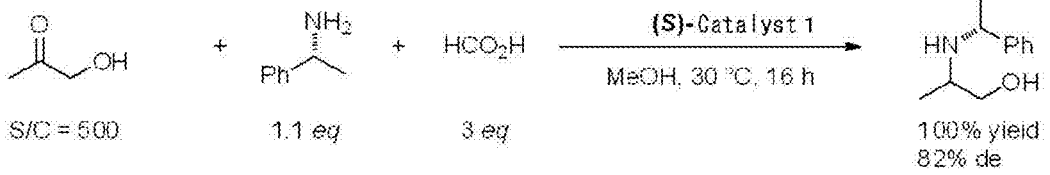
Figure 6:
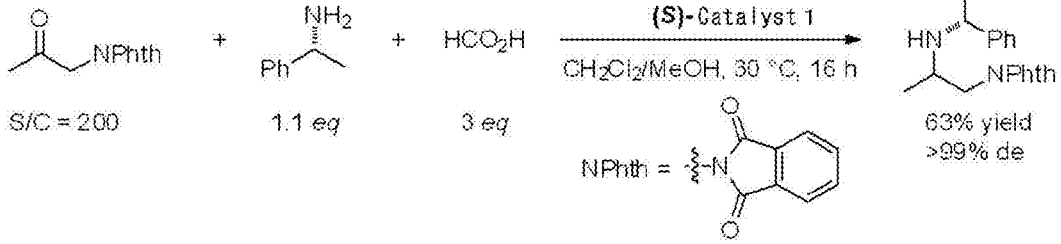
Figure 7:
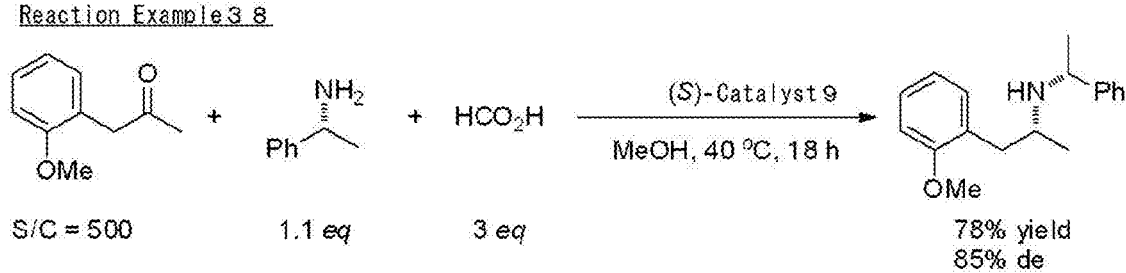
FIG. 7 shows reaction formulae of Reaction Examples 38 to 40.
Figure 7:
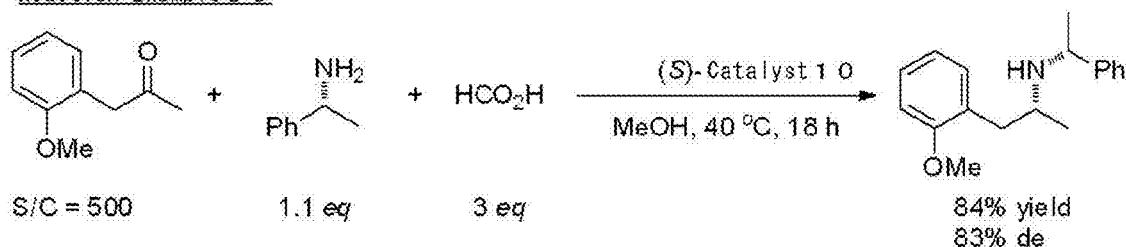
Figure 7:
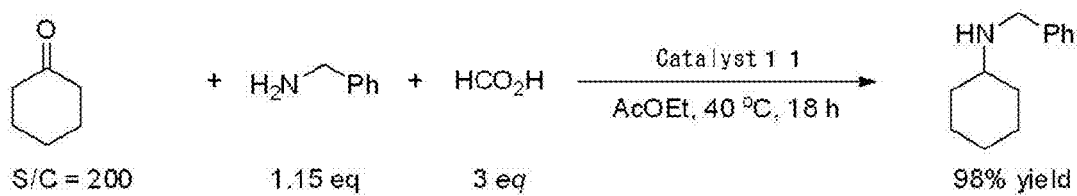

Below, the present invention is described in detail. In one aspect, the present invention relates to an organometallic compound of general formula (1):

[Formula 12]

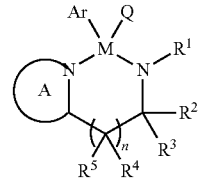

(1)

Ar is typically a cyclopentadienyl group or an aromatic compound, in which one or more hydrogen atoms may be substituted by a substituent, preferably by a substituent W. Specific examples of Ar include, but are not limited to, for example, unsubstituted benzene, toluene, o-, m- and p-xylene, o-, m- and p-cymene, 1,2,3-, 1,2,4- and 1,3,5-trimethylbenzene, 1,2,4,5-tetramethylbenzene, 1,2,3,4-tetramethylbenzene, 1,3,4,5-tetramethylbenzene, pentamethylbenzene, and benzene having alkyl groups such as hexamethylbenzene, benzene having unsaturated hydrocarbon groups such as benzyl, vinyl and allyl, and benzene having heteroatoms such as hydroxyl group, alkoxy group, ester group, amino group and halogen group, etc. The number of substituents on the benzene ring is any number from 1 to 6, and arbitrary positions may be selected as substitution positions. In terms of easiness in the synthesis of complex, Ar is preferably p-cymene, 1,3,5-trimethylbenzene, and hexamethylbenzene.

In addition, examples of cyclopentadienyl group which may have a substituent include, but are not limited to, cyclopentadienyl group, methylcyclopentadienyl group, ethylcyclopentadienyl group, isopropylcyclopentadienyl group, phenylcyclopentadienyl group, benzylcyclopentadienyl group, 1,2-dimethylcyclopentadienyl group, 1,3-dimethylcyclopentadienyl group, 1,2,3-trimethylcyclopentadienyl group, 1,2,4-trimethylcyclopentadienyl group, 1,2,3,4-tetramethylcyclopentadienyl group, 1,2,3,4,5-pentamethylcyclopentadienyl group (Cp*), etc. In terms of easiness in the synthesis of complex, it is preferably 1,2,3,4,5-pentamethylcyclopentadienyl group (Cp*).

The substituent W is, typically a saturated or unsaturated hydrocarbon group, an aryl group in which a carbon atom may be replaced by a heteroatom, a heterocyclyl group, an alkoxy group, a fluoroalkyl group, an acyl group, an ester group, a hydroxyl group, an amino group, an amide group, a carboxyl group, a sulfonyl group, a nitro group, a cyano group, a phosphino group, a sulfenyl group, a sulfo group, a mercapto group, a phosphino group, a silyl group or a halogen group, and in particular, it is a saturated or unsaturated C1-C20 hydrocarbon group, a 6- to 20-membered aryl group in which a carbon atom may be replaced by a heteroatom, a 3- to 20-membered heterocyclyl group, a C1-C20 alkoxy group, —C(=O)—$R^a$, —C(=O)—O$R^a$, a hydroxyl group, —N$R^a R^b$, —C(=O)—N$R^a R^b$, a nitro group, a cyano group, —P$R^a R^b$, a C1-C20 sulfenyl group, a sulfo group, a mercapto group, —Si$R^a R^b R^c$, a halogen group or —S(=O)$_2$—$R^a$, $R^a$, $R^b$ and $R^c$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom.

As used herein, "hydrocarbon group" and "hydrocarbyl group" are used interchangeably, and they mean a substituent consisting of a carbon backbone and a hydrogen atom attached thereto, and they include a saturated or unsaturated linear or cyclic hydrocarbon group. Examples of saturated or unsaturated linear hydrocarbon group include saturated or unsaturated linear or branched alkyl group, and examples of saturated or unsaturated cyclic hydrocarbon group include saturated or unsaturated cycloalkyl group and aryl group.

As used herein, "saturated or unsaturated alkyl group" includes saturated straight or branched chain alkyl groups, and unsaturated straight or branched chain alkyl groups such as alkynyl group and alkenyl group. When it is described simply as "alkyl group", unless otherwise indicated, it means a "saturated or unsaturated alkyl group". As an alkyl group, C1-C20 alkyl groups are preferred, C1-C10 alkyl groups are more preferred, and C1-C5 alkyl groups are furthermore preferred.

As used herein, "saturated or unsaturated cycloalkyl group" includes saturated cycloalkyl group and unsaturated cycloalkenyl group. When it is described simply as "cycloalkyl group", unless otherwise indicated, it means a "saturated or unsaturated cycloalkyl group". As a cycloalkyl group, C3-C20 cycloalkyl groups are preferred, and C5-C10 cycloalkyl groups are more preferred.

As used herein, "heterocyclyl group" includes a group in which one or more carbon atoms of a saturated or unsaturated cycloalkyl group are replaced by heteroatoms such as nitrogen atom, oxygen atom and sulfur atom.

As used herein, for example, the expression of "a 6- to 20-membered aryl group in which a carbon atom may be replaced by a heteroatom" includes a 6- to 20-membered heteroaromatic group in which one or more carbon atoms in the aromatic hydrocarbon group are replaced by one or more heteroatoms selected from nitrogen atom, oxygen atom and sulfur atom, etc. Such heteroaromatic group may be specifically referred to as "heteroaryl group".

As used herein, "aralkyl group" means a group in which one hydrogen atom of the above alkyl group is substituted by an aryl group, and a carbon atom of said aryl may be replaced by a heteroatom.

As used herein, "alkylaryl" includes aryl groups in which one or more hydrogen atoms of the aryl group are substituted by an alkyl group, and a carbon atom of the aryl may be replaced by a heteroatom.

Specific examples of W include, but are not limited to, phenyl group, naphthyl group, methyl group, ethyl group, n-propyl group, i-propyl group, n-butyl group, i-butyl, n-pentyl group, cyclopentyl group, n-hexyl group, cyclohexyl group, cyclohexylene group, vinyl group, propenyl group, butenyl group, phenyl group, toluyl group, naphthyl group, pyridyl group, furanyl group, methoxy group, ethoxy group, propoxy group, acetyl group, propanoyl group, cyclohexanecarbonyl group, benzoyl group, methoxycarbonyl group, ethoxycarbonyl group, hydroxyl group, methylamino group, ethylamino group, i-propylamino group, dimethylamino group, diethylamino group, diisopropylamino group, fluoro group, bromo group, chloro group, iodo group, methanesulfonyl group, ethanesulfonyl group, p-toluenesulfonyl group, methylsilyl group, dimethylsilyl group, trimethylsilyl group, trifluoromethyl group, diphenylphosphino group, dicyclohexylphosphino group, cyclopropylphosphino group, cyclobutylphosphino group, cyclopentylphosphino group, cyclohexylphosphino group, etc. In terms of easiness in the synthesis of complex, W is preferably a saturated or unsaturated hydrocarbon group, and more preferably methyl group and i-propyl group.

M in general formula (1) is either ruthenium, rhodium or iridium. From the viewpoint of high catalytic activity, rhodium or iridium is preferred.

Q in general formula (1) is a hydride group or an anionic group. Specific examples of Q include, but are not limited to, hydride group, hydroxy group, alkoxy group, cross-linked oxo group, fluoro group, bromo group, chloro group, iodo group, tetrafluoroborate group, tetrahydroborate group, tetrakis pentafluorophenyl borate group, tetrakis[3',5'-bis(trifluoromethyl)phenyl]borate group, hexafluorophosphate group, hexafluoroantimonate group, hexachloroantimonate group, hexafluoroarsenate group, perchlorate group, acetoxy group, benzoyloxy group, (2',6'-dihydroxybenzoyl)oxy group, (2',5'-dihydroxybenzoyl)oxy group, (3'-aminobenzoyl)oxy group, (2',6'-dimethoxybenzoyl)oxy group, (2',4',6'-triisopropylbenzoyl)oxy group, 1-naphthalene carboxylate group, 2-naphthalene carboxylate group, trifluoroacetoxy group, trifluoromethane sulfonimide group, nitromethyl group, nitroethyl group, toluenesulfonate group, methanesulfonate group, ethanesulfonate group, n-propanesulfonate group, isopropanesulfonate group, n-butanesulfonate group, fluorosulfonate group, fluoromethanesulfonate group, difluoromethanesulfonate group, trifluoromethanesulfonate group, pentafluoroethanesulfonate group, phosphate group, (S)-(+)-2,2'-dihydroxy-1,1'-binaphthyl phosphate group, (R)-(−)-2,2'-dihydroxy-1,1'-binaphthyl phosphate group, etc. In terms of easiness in the synthesis of complex, Q is preferably chloro group, bromo group, iodo group, and trifluoromethanesulfonate group.

In addition, M may be coordinated with coordination neutral molecule, in addition to the anionic group Q. Specific examples of molecules coordinated to M include water, alcohols such as methanol, ethanol, n-propanol, isopropanol and 2-methoxyethanol, tetrahydrofuran, ethers such as diethyl ether, diisopropyl ether, cyclopentyl methyl ether, methyl-tert-butyl ether, N,N'-dimethylformamide, N,N'-dimethylacetamide, N-methyl-2-pyrrolidone, dimethyl sulfoxide, acetone, chloroform, acetonitrile, benzonitrile, pyridine, trialkylphosphines such as trimethylphosphine, triethylphosphine or tricyclohexyl, triarylphosphines such as triphenylphosphine, etc. If such a neutral molecule is coordinated, a cationic complex is formed, and the anionic group is to be present as a counter anion.

$R^1$ is not particularly limited as long as it is an electron-withdrawing group. The electron-withdrawing group in the present invention is a substituent having electron withdrawing properties by electronic effects, and is a substituent exhibiting positive σp value, that is a Hammett's substituent constant indicating measures of electron-withdrawing or electron-donating properties of a substituent. Typically, $R^1$ is —S(=O)$_2$—$R^a$, a 6- to 20-membered aryl group in which a carbon atom may be replaced by a heteroatom, —C(=O)—OR$^a$, —C(=O)—R$^a$, —C(=O)—NR$^a$R$^b$, —C(=S)—NR$^a$R$^b$, a C1-C20 sulfenyl group or a perfluoroalkyl group, wherein one or more hydrogen atoms of these groups may be substituted by a substituent, preferably by a substituent W. Typically R$^a$ and R$^b$ are, each independently, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom.

Especially from the viewpoint of reactivity and diastereoselectivity, $R^1$ is preferably —S(=O)$_2$—$R^a$, —C(=O)—OR$^a$, or —C(=O)—NR$^a$R$^b$, in which one or more hydrogen atoms of these groups may be substituted by a substituent W.

Since the substituent R$^1$ is an electron-withdrawing group, decomposition of the complex by detachment of ligands under acidic conditions is considered be suppressed. As a result, it is believed that high catalytic activity and diastereoselectivity can be achieved.

Specific examples R$^1$ include, but are not limited to, methanesulfonyl group (Ms), ethanesulfonyl group (Es), n-propylsulfonyl group, i-propylsulfonyl group, n-butylsulfonyl group, i-butylsulfonyl group, n-pentylsulfonyl group, cyclopentylsulfonyl group, 1-octanesulfonyl group, 1-hexadecanesulfonyl group, o-toluenesulfonyl group, m-toluenesulfonyl group, p-toluenesulfonyl group (Ts), benzenesulfonyl group, 2,6-dimethylbenzenesulfonyl group, 3,5-dimethylbenzenesulfonyl group, 2,4,6-trimethylbenzeneulfonyl group, 2,4,6-triisopropylbenzenesulfonyl group, 4-cyanobenzenesulfonyl group, 2-nitrobenzenesulfonyl group, 3-nitrobenzenesulfonyl group, 4-nitrobenzenesulfonyl group, 2,4-dinitrobenzenesulfonyl group, 2-(trifluoromethyl)benzenesulfonyl group, 4-(trifluoromethyl)benzenesulfonyl group, 3,5-bis(trifluoromethyl)benzenesulfonyl group, 4-chlorobenzenesulfonyl group, 2,4-dichlorobenzenesulfonyl group, 4-fluorobenzenesulfonyl group, 3,4,5-trifluorobenzenesulfonyl group, 2,3,4,5,6-pentafluorobenzenesulfonyl group, 4-methoxybenzenesulfonyl group, (+)-10-camphorsulfonyl group, (-)-10-camphorsulfonyl group, pyridine-3-sulfonyl group, trichloromethanesulfonyl group, trifluoromethanesulfonyl group, 2,2,2-trifluoroethanesulfonyl group, 4-hydroxybenzenesulfonyl group, 4-biphenylbenzenesulfonyl group, benzylsulfonyl group (—SO$_2$Bn), phenyl group, 4-nitrophenyl group, 4-cyanophenyl group, 4-fluorophenyl group, 3,5-difluorophenyl group, 3,4,5-trifluorophenyl group, 4-(trifluoromethyl)phenyl group, 3,5-bis(trifluoromethyl)phenyl group, pentafluorophenyl group, —CF$_3$, —CF$_2$CF$_3$, —CO—CH$_3$, —CO—CH$_2$CH$_3$, —CO—CH(CH$_3$)$_2$, —CO—C(CH$_3$)$_3$, —CO-Ph, —CO$_2$CH$_3$, —CO$_2$CH$_2$CH$_3$, —CO$_2$CH(CH$_3$)$_2$, —CO$_2$C(CH$_3$)$_3$, —CO$_2$Ph, —CO—CF$_3$, —CO—CF$_2$CF$_3$, —CO—CCl$_3$, —CO—CH$_2$CF$_3$, —CO—CH$_2$CCl$_3$, —CO—CH$_2$CCl$_3$, —CO$_2$CH$_2$CF$_3$, —CO$_2$CF$_3$, —CO$_2$CF$_2$CF$_3$, —CO$_2$CH$_2$CCl$_3$, —CO$_2$CCl$_2$CCl$_3$, —CO$_2$CF$_3$, —C(=O)NHCH$_3$, —C(=O)NHCH$_2$CH$_3$, —C(=O)NHCH(CH$_3$)2, —C(=O)NHC(CH$_3$)$_3$, —C(=O)NHCF$_3$, —C(=O)NHPh, —C(=O)NH-(4-F—C$_6$H$_4$), —C(=O)NH-(4-CN—C$_6$H$_4$), —C(=O)NH-(4-NO$_2$—C$_6$H$_4$), —C(=O)NH-(4-CF$_3$—C$_6$H$_4$), —C(=O)NH-(3,5-(CF$_3$)$_2$—C$_6$H$_3$), —C(=O)NH-(3,5-F$_2$—C$_6$H$_3$), —C(=O)NH-(3,4,5-F$_3$—C$_6$H$_3$), —C(=O)NHCH$_3$, —C(=O)NHCH$_3$, etc. From the viewpoint of catalytic activity, high reaction yield and diastereoselectivity, R$^1$ is preferably —S(=O)—R$^a$, a 6- to 20-membered aryl group in which a carbon atom may be replaced by a heteroatom, —C(=O)—R$^a$, —C(=O)—NR$^a$R$^b$, and particularly preferably methanesulfonyl group, ethanesulfonyl group, p-toluenesulfonyl group, benzyl sulfonyl group, acetyl group, and —C(=O)NHPh.

R$^2$, R$^3$, R$^4$ and R$^5$ are, typically and independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a C1-C20 alkoxy group, —C(=O)—OR$^a$, a C1-C20 fluoroalkyl group, —C(=O)—R$^a$, —S(=O)$_2$—R$^a$, a hydroxyl group, —NR$^a$R$^b$, —C(=O)—NR$^a$R$^b$, a C1-C20 sulfenyl group, or —SiR$^a$R$^b$R$^c$, wherein one or more hydrogen atoms of these groups may be substituted by the substituent W.

R$^a$, R$^b$ and R$^c$ are, typically and independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom.

Specific examples of R$^2$, R$^3$, R$^4$ and R$^5$ include, but are not limited to, hydrogen atom, methyl group, ethyl group, n-propyl group, i-propyl, tert-butyl group, isobutyl group, benzyl group, cyclohexyl group, phenyl group, pyridyl group, vinyl group, ethynyl group, a group having an ester bond, acetyl group, benzoyl group, methanesulfonyl group, ethanesulfonyl group, p-toluenesulfonyl group, trifluoromethanesulfonyl group, methylsilyl group, dimethylsilyl group, and trimethylsilyl group, etc. From the viewpoint of catalytic activity and high reaction yield, they are preferably hydrogen atom, methyl group, isopropyl group, tert-butyl group, isobutyl group, benzyl group, phenyl group, 4-methoxyphenyl group, 4-(dimethylamino)phenyl group, l-naphthyl group, 2-naphthyl group, anthracenyl group, fluorenyl group, phenalenyl group, phenanthrenyl group, and indenyl group, etc.

R$^2$ and R$^3$ and/or R$^4$ and R$^5$ may be bonded to each other to form a ring.

R$^1$ and R$^2$, or R$^1$ and R$^3$ may be bonded to each other to form a ring.

One of R$^2$ and R$^3$, and one of R$^4$ and R$^5$ may be bonded to each other to form a ring, and when the formed ring represents an aromatic compound, then the bond between the carbon atom to which R$^2$ and R$^3$ are bonded, and the carbon atom to which R$^4$ and R$^5$ are bonded, is a double bond, and R$^2$ or R$^3$ and R$^4$ or R$^5$ which are not involved in the ring formation are unsubstituted.

The carbon atoms to which R$^2$ and R$^3$ are bonded, and/or the carbon atom to which R$^4$ and R$^5$ are bonded may be asymmetric carbon atoms, and from the viewpoint of high enantioselectivity and diastereoselectivity, they are preferably asymmetric carbon atoms.

n is typically an integer of 0 or 1, and is preferably 1.

A is typically a saturated or unsaturated heterocycle containing at least one nitrogen atom, wherein one or more hydrogen atoms in the ring may be substituted by a substituent W.

Heterocycle A may be monocyclic or polycyclic.

For example, examples of the monocyclic heterocycle A include, but are not limited to, a 4- to 7-membered, preferably 5- to 6-membered saturated or unsaturated heterocycle having only one nitrogen atom as a ring member heteroatom, and a 4- to 7-membered, preferably 5- to 6-membered saturated or unsaturated heterocycle having, in addition to one nitrogen atom, one or more heteroatoms selected from nitrogen atom, oxygen atom and sulfur atom, etc. Examples of the polycyclic heterocycle A include, but are not limited to the following: the above-mentioned monocyclic heterocycle A to which one or more of monocyclic or polycyclic saturated or unsaturated hydrocarbon rings, or monocyclic or polycyclic saturated or unsaturated heterocycles are fused to form a saturated or unsaturated heterocycle, and preferably 2 to 5, more preferably 2 to 3 rings are fused to form a saturated or unsaturated heterocycle. Preferably, A is a monocyclic or polycyclic aromatic ring.

Specific examples of A include, in addition to 6-membered nitrogen-containing monocyclic aromatic rings such as pyridine ring, pyridazine ring, pyrazine ring, pyrimidine ring, triazine ring and tetrazine ring, polycyclic aromatic groups containing 6-membered nitrogen-containing aromatic ring structure, such as quinoline ring and isoquinoline ring, quinazoline ring, quinoxaline ring, acridine ring, cinnoline ring, phthalazine ring, naphthyridine ring, etc. In addition, it is suitable that such groups comprise nitrogen-containing aromatic ring structures, and the examples include 5,6,7,8-tetrahydroquinolyl group, etc. Examples of 5-membered nitrogen-containing ring include pyrazole ring, isoxazole ring, isothiazole ring, imidazole ring, oxazole ring, thiazole ring, 1,2,3-triazole ring, 1,2,4-triazole ring, and tetrazole ring, etc.

Examples of the group containing non-aromatic nitrogen-containing ring structure include, 4-membered nitrogen-containing rings such as azetidine ring, 5-membered nitrogen-containing rings or a group containing thereof such as pyrrolidine ring, pyrroline ring, imidazolidine ring, imidazoline ring, pyrazolidine ring, pyrazoline ring, oxazoline ring, indoline ring and isoindoline ring, and 6-membered nitrogen-containing rings or a group containing thereof such as piperidine ring, piperazine ring, morpholine ring and quinuclidine ring, etc.

One aspect of the present invention relates to an organometallic compound of general formula (1) that is an optically active substance. By using the optically active organometallic compound of general formula (1), high-yield and highly-diastereoselective reaction can be proceeded using inexpensive optically active amine with a small amount of catalyst of, for example, S/C=500 or more.

In terms of high catalytic activity and high diastereoselectivity, a compound of general formula (1-a):

[Formula 13]

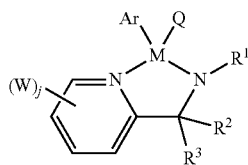

(1-a)

or of general formula (1-b):

[Formula 14]

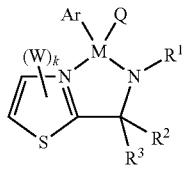

(1-b)

is preferred.

In the above formulae,
Ar, Q and M are as defined above.
$R^1$ is $-S(=O)_2-R^a$, a 6- to 20-membered aryl group in which a carbon atom may be replaced by a heteroatom, $-C(=O)-OR^a$, $-C(=O)-R^a$, $-C(=O)-NR^aR^b$, $-C(=S)-NR^aR^b$, a C1-C20 sulfenyl group or a perfluoroalkyl group, $R^1$ is preferably $-S(=O)_2-R^a$ or a 6- to 20-membered aryl group in which a carbon atom may be replaced by a heteroatom, and particularly preferably mesyl group (Ms), tosyl group (Ts), benzylsulfonyl group ($-SO_2Bn$), acetyl group, or $-C(=O)NHPh$.

$R^2$ and $R^3$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a C1-C20 alkoxy group, $-C(=O)-OR^a$, a C1-C20 fluoroalkyl group, $-C(=O)-R^a$, $-S(=O)_2-R^a$, a hydroxyl group, $-NR^aR^b$, $-C(=O)-NR^aR^b$, a C1-C20 sulfenyl group, or $-SiR^aR^bR^c$, wherein one or more hydrogen atoms of these groups may be substituted by the substituent W, and preferably, $R^2$ and $R^3$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, or a 6- to 20-membered alkylaryl group in which a carbon atom of the aryl may be replaced by a heteroatom.

The carbon atom to which $R^2$ and $R^3$ are bonded is an asymmetric carbon atom.

$R^2$ and $R^3$ are as follows: preferably one of them is hydrogen atom, and the other is a saturated or unsaturated C1-C21 alkyl group or a saturated or unsaturated C3-C10 cycloalkyl group both of which may be substituted by a substituent W, or a 6- to 20-membered aryl group in which a carbon atom may be replaced by a heteroatom, or a 3- to 10-membered heterocyclyl group, and is particularly preferably C1-C6 alkyl or a 6- to 20-membered aryl group in which a carbon atom may be replaced by a heteroatom.

A plurality of substituents W may be introduced into A, and the number of substitution j is an integer of 0-4, and k is an integer of 0-2.

The substituent W to be introduced into A has the same meaning as mentioned above, and specific examples include methyl group, ethyl group, n-propyl group, i-propyl, tert-butyl group, cyclohexyl group, phenyl group, pyridyl group, vinyl group, ethynyl group, a group having ester bond, acetyl group, methoxy group, ethoxy group, isopropoxy group, dimethylamino group, diethylamino group, nitro group, cyano group, trifluoromethyl group, fluoro group, chloro group, bromo group, methanesulfonyl group, ethanesulfonyl group, p-toluenesulfonyl group, and trimethylsilyl group, etc., but they are not limited thereto. In terms of high catalytic activity, W is preferably methyl group, ethyl group, and propyl group.

The compound represented by general formula (1) can be obtained as racemates or as optically active forms. When producing optically active amines, the use of a compound of general formula (1) in an optically active form is preferred from the standpoint of highly efficient production.

One aspect of the present invention relates to a catalyst used for a reducing reaction or a hydrogenation reaction of one or more kinds selected from the group consisting of imine, iminium cation and enamine, or for a reducing reaction or a hydrogenation reaction of one or more kinds selected from the group consisting of imine, iminium cation and enamine that are generated in a system of mixing a carbonyl compound and an amine compound, wherein the catalyst comprises at least one organometallic compound of general formula (1). Naturally, the organometallic compound of general formula (1) per se can be used as a catalyst, thus the invention includes an embodiment wherein an organometallic compound of general formula (1) is used as a catalyst.

As used herein, "imine" means a compound having carbon-nitrogen double bond, and iminium cation means an iminium ion wherein a proton or an organic cation is bonded to the imine nitrogen.

As used herein, "enamine" means a compound in which an amino group is present on the carbon of the double bond.

Imine and enamine which have hydrogen on the α-carbon are generally tautomeric, and each word may include tautomeric forms unless otherwise stated.

It is possible to produce an amine compound by diastereoselective reduction of previously-prepared imine or enamine, or of one or more kinds selected from the group consisting of imine, iminium cation and enamine that have been generated in a system of mixing a carbonyl compound and an amine compound, using hydrogen gas or a hydrogen-donating organic or inorganic compound.

As long as it does not adversely affect the catalytic activity and diastereoselectivity or enantioselectivity, other suitable catalysts may be used in the present invention in order to promote the reaction, in addition to the catalyst of the present invention; for example, an acid catalyst may be used for the generation of imine or enamine in the system.

Examples of imine include, but are not limited to, a compound of general formula (2):

[Formula 15]

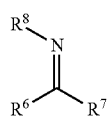

(2)

In general formula (2), $R^6$ and $R^7$ are, independently of one another, a hydrogen atom, a hydrocarbyl group, an aryl group in which a carbon atom may be replaced by a heteroatom, a 6- to 20-membered alkylaryl group in which a carbon atom of the aryl may be replaced by a heteroatom, a 6- to 20-membered aralkyl group in which a carbon atom of the aryl may be replaced by a heteroatom, a heterocyclyl group, a carboxyl group, an ester group or an acyl group, wherein one or more hydrogen atoms of these groups may be substituted by a substituent W. Examples of ester group include a group represented by —C(=O)—OR$^a$, and examples of acyl group include a group represented by —C(=O)—R$^a$.

Specific examples include, but are not limited to, alkyl groups such as methyl, ethyl, propyl, butyl, pentyl, hexyl, heptyl, etc., fluoroalkyl groups such as trifluoromethyl group, cycloalkyl groups such as cyclopropyl, cyclobutyl, cyclopentyl, cyclohexyl, etc., unsaturated hydrocarbons such as vinyl, allyl, etc., aromatic monocyclic or polycyclic groups such as phenyl, 1-naphthyl, 2-naphthyl, anthracenyl group, fluorenyl group, phenalenyl group, phenanthrenyl group, indenyl group, etc., heteromonocyclic or polycyclic groups such as thienyl, furyl, pyranyl, xanthenyl, pyridyl, pyrrolyl, imidazolinyl, indolyl, carbazolyl, phenanthrolinyl, etc., ester groups such as ferrocenyl group, carboxylic acid, methoxycarbonyl group, ethoxycarbonyl group, etc., acyl groups such as formyl group, acetyl group, benzoyl group, etc.

$R^8$ is a hydrogen atom, a hydroxyl group, a hydrocarbyl group, an aryl group in which a carbon atom may be replaced by a heteroatom, a 6- to 20-membered alkylaryl group in which a carbon atom of the aryl may be replaced by a heteroatom, a 6- to 20-membered aralkyl group in which a carbon atom of the aryl may be replaced by a heteroatom, a heterocyclyl group, a sulfonyl group, an alkoxy group, an acyl group, an ester group, a carboxyl group, a phosphinyl group, a sulfinyl group or a silyl group, wherein one or more hydrogen atoms of these groups may be substituted by a substituent W. Examples of sulfony group include —S(=O)$_2$—R$^a$, examples of acyl group include —C(=O)—R$^a$, examples of ester group include C(=O)—OR$^a$, examples of phosphinyl group include —P(=O)R$^a$R$^b$, examples of sulfinyl group include —S(=O)—R$^a$, and examples of silyl group include —SiR$^a$R$^b$R$^c$, etc.

Specific examples include, but are not limited to, alkyl groups such as methyl, ethyl, propyl, butyl, pentyl, hexyl, heptyl, etc., cycloalkyl groups such as cyclopropyl, cyclobutyl, cyclopentyl, cyclohexyl, etc., unsaturated hydrocarbons such as vinyl, allyl, etc., aromatic monocyclic or polycyclic groups such as phenyl, 1-naphthyl, 2-naphthyl, anthryl, phenanthryl, indenyl, etc., heteromonocyclic or polycyclic groups such as thienyl, furyl, pyranyl, xanthenyl, pyridyl, pyrrolyl, imidazolinyl, indolyl, carbazolyl, phenanthrolinyl, etc., and ferrocenyl group, etc.

$R^6$ and $R^7$ or $R^6$ and $R^8$ may be bonded to each other to form a ring. The ring may be either monocyclic or polycyclic.

When $R^6$ and $R^7$ form a ring, they may form, without limitation, a saturated or unsaturated cyclic hydrocarbon, a heteromonocyclic ring or polycyclic ring comprising heteroatoms such as nitrogen, oxygen, and sulfur atoms, etc., wherein one or more carbons of the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include cycloalkanes such as cyclopentane ring, cyclohexane ring, and cycloheptane ring, which may have said substituent, 2,3-dihydro-1H-indene ring, or aryl-fused cycloalkanes such as 1,2,3,4-tetrahydronaphthalene ring, etc. which may have said substituent, and polycyclic alicyclic hydrocarbons such as decahydronaphthalene, etc.

When $R^6$ and $R^8$ are bonded to form a ring, it may be, without limitation, for example an unsaturated heterocycle, wherein one or more carbons of the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include 3,4-dihydro-2H-pyrrole and, alicyclic heterocycles such as 2,3,4,5-tetrahydropyridine, as well as pyridine, quinoline, and heterocyclic aromatic rings such as isoquinoline, etc.

Examples of the substituent may have various types such as a substituent W, and include hydrocarbon groups such as alkyl, alkenyl, cycloalkyl, cycloalkenyl, etc., a fluoroalkyl group, a halogen atom, oxygen-containing groups such as hydroxyl group, acyl group, alkoxy group, carboxyl group, ester group, etc., an amino group, an amide group, a sulfonyl group, a sulfenyl group, a sulfo group, a mercapto group, a silyl group, a nitro group, and a cyano group, etc.

Iminium cation includes, for example, a cation of general formula (3):

[Formula 16]

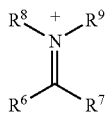

(3)

but it is not limited thereto.

Regarding general formula (3), $R^6$ and $R^7$ represent the same meanings as defined above, $R^8$ and $R^9$ are, independently of one another, a hydrogen atom, a hydroxyl group, a hydrocarbyl group, an aryl group in which a carbon atom may be replaced by a heteroatom, a 6- to 20-membered alkylaryl group in which a carbon atom of the aryl may be replaced by a heteroatom, a 6- to 20-membered aralkyl group in which a carbon atom of the aryl may be replaced by a heteroatom, a heterocyclyl group, a sulfonyl group, an alkoxy group, an acyl group, an ester group, a carboxyl group, a phosphinyl group, a sulfinyl group or a silyl group, wherein one or more hydrogen atoms of these groups may be substituted by any substituent. Examples of acyl group include —C(=O)—$R^a$, examples of ester group include —C(=O)—$OR^a$, examples of phosphinyl group include —P(=O)$R^aR^b$, examples of sulfinyl group include —S(=O)—$R^a$, and examples of silyl group include —$SiR^aR^bR^c$, etc.

Specific examples include, but are not limited to, alkyl groups such as methyl, ethyl, propyl, butyl, pentyl, hexyl, heptyl, etc., cycloalkyl groups such as cyclopropyl, cyclobutyl, cyclopentyl, cyclohexyl, etc., unsaturated hydrocarbons such as vinyl, allyl, etc., aromatic monocyclic or polycyclic groups such as phenyl, 1-naphthyl, 2-naphthyl, anthryl, phenanthryl, indenyl, etc., heteromonocyclic or polycyclic groups such as thienyl, furyl, pyranyl, xanthenyl, pyridyl, pyrrolyl, imidazolinyl, indolyl, carbazolyl, phenanthrolinyl, etc., and ferrocenyl group, etc.

One or more selected from $R^6$ and $R^7$, $R^6$ and $R^8$, $R^7$ and $R^9$, and $R^8$ and $R^9$, may be bonded to each other to form a ring. The ring may be either monocyclic or polycyclic.

When $R^6$ and $R^7$ form a ring, they may form, without limitation, a saturated or unsaturated cyclic hydrocarbon, a heteromonocyclic ring or polycyclic ring comprising heteroatoms such as nitrogen, oxygen, and sulfur atoms, etc., wherein one or more carbons of the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include cycloalkanes such as cyclopentane ring, cyclohexane ring, and cycloheptane ring, which may have said substituent, 2,3-dihydro-1H-indene ring, or aryl-fused cycloalkanes such as 1,2,3,4-tetrahydronaphthalene ring, etc. which may have said substituent, and polycyclic alicyclic hydrocarbons such as decahydronaphthalene, etc.

When $R^6$ and $R^8$ and/or $R^7$ and $R^9$ are bonded to form a ring, it may be, without limitation, for example an unsaturated heterocycle, wherein one or more carbons of the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include 3,4-dihydro-2H-pyrrole and, alicyclic heterocycles such as 2,3,4,5-tetrahydropyridine, as well as pyridine, quinoline, and heterocyclic aromatic rings such as isoquinoline, etc.

When $R^8$ and $R^9$ are bonded to form a ring, it may be, without limitation, for example a saturated or unsaturated heterocycle, wherein one or more carbons of the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include pyrrolidine, piperidine, and alicyclic heterocycles such as azepane, which may have said substituent.

Examples of the substituent may have various types such as a substituent W, and include hydrocarbon groups such as alkyl, alkenyl, cycloalkyl, cycloalkenyl, etc., a fluoroalkyl group, a halogen atom, oxygen-containing groups such as hydroxyl group, acyl group, alkoxy group, carboxyl group, ester group, etc., an amino group, an amide group, a sulfonyl group, a sulfenyl group, a sulfo group, a mercapto group, a silyl group, a nitro group, and a cyano group, etc.

Enamine includes, for example, a compound of general formula (4):

[Formula 17]

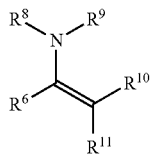

(4)

but it is not limited thereto.

It may also be an enaminium cation formed by protonation of enamine of general formula (4) on the nitrogen.

Regarding general formula (4), $R^6$, $R^8$ and $R^9$ represent the same meanings as indicated above.

$R^{10}$ and $R^{11}$ are, independently of one another, a hydrogen atom, a hydrocarbyl group, an aryl group in which a carbon atom may be replaced by a heteroatom, a heterocyclyl group, a carboxyl group, an ester group or an acyl group, wherein one or more hydrogen atoms may be substituted by any substituent. Examples of ester group include a group represented by —C(=O)—$OR^a$, and examples of acyl group include a group represented by —C(=O)—$R^a$, etc.

Specific examples include, but are not limited to, alkyl groups such as methyl, ethyl, propyl, butyl, pentyl, hexyl, heptyl, etc., fluoroalkyl groups such as trifluoromethyl group, cycloalkyl groups such as cyclopropyl, cyclobutyl, cyclopentyl, cyclohexyl, etc., unsaturated hydrocarbons such as vinyl, allyl, etc., aromatic monocyclic or polycyclic groups such as phenyl, 1-naphthyl, 2-naphthyl, anthracenyl group, fluorenyl group, phenalenyl group, phenanthrenyl group, indenyl group, etc., heteromonocyclic or polycyclic groups such as thienyl, furyl, pyranyl, xanthenyl, pyridyl, pyrrolyl, imidazolinyl, indolyl, carbazolyl, phenanthrolinyl, etc., ester groups such as ferrocenyl group, carboxyl group, methoxycarbonyl group, ethoxycarbonyl group, etc., acyl groups such as formyl group, acetyl group, benzoyl group, etc.

One or more selected from $R^6$ and $R^8$, $R^6$ and $R^{11}$, $R^8$ and $R^9$, $R^9$ and $R^{10}$, and $R^{10}$ and $R^{11}$, may be bonded to each other to form a ring. The ring may be either monocyclic or polycyclic.

When $R^6$ and $R^{11}$ form a ring, they may form, without limitation, a saturated or unsaturated cyclic hydrocarbon, a heteromonocyclic ring or polycyclic ring comprising heteroatoms such as nitrogen, oxygen, and sulfur atoms, etc., wherein one or more carbons of the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include cyclopentene ring and cyclohexene ring which may have said substituent, unsaturated alicyclic hydrocarbons such as cycloheptene ring, aryl-fused cycloalkenes such as 1,4-dihydronaphthalene, unsaturated heterocycles such as 1,2,3,6-tetrahydropyridine, which may have said substituent.

When $R^6$ and $R^8$ are bonded to form a ring, it may be, without limitation, for example an unsaturated heterocycle, wherein one or more carbons of the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include 3,4-dihydro-2H-pyrrole and, alicyclic heterocycles such as 2,3,4,5-tetrahydropyridine, as well as pyridine, quinoline, and heterocyclic aromatic rings such as isoquinoline, etc.

When $R^8$ and $R^9$ are bonded to form a ring, it may be, without limitation, for example a saturated or unsaturated heterocycle, wherein one or more carbons of the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include pyrrolidine, piperidine, and alicyclic heterocycles such as azepane, which may have said substituent.

When $R^{10}$ and $R^{11}$ form a ring, they may form, without limitation, a saturated or unsaturated cyclic hydrocarbon, a heteromonocyclic ring or polycyclic ring comprising heteroatoms such as nitrogen, oxygen, and sulfur atoms, etc., wherein one or more carbons of the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include cycloalkanes such as cyclopentane ring, cyclohexane ring, and cycloheptane ring, which may have said substituent, 2,3-dihydro-1H-indene ring, or aryl-fused cycloalkanes such as 1,2,3,4-tetrahydronaphthalene ring, etc. which may have said substituent, and polycyclic alicyclic hydrocarbons such as decahydronaphthalene, etc.

When $R^9$ and $R^{10}$ are bonded to form a ring, it may be for example an unsaturated heterocycle, wherein one or more carbons in the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include unsaturated heterocycles such as 1,2,3,4-tetrahydropyridine that may have a substituent.

To carry out the reaction with higher diastereoselectivity, a cyclic enamine having a substituent in the side chain is preferable, and the examples include optically active N-(1-phenylethyl)-3,4-dihydronaphthalen-2-amine, etc.

Regarding the above-mentioned imine, iminium cation and enamine, in order to carry out the reaction at a higher diastereoselectivity, imines, iminium cations and enamines derived from cyclic ketones having a substituent on the side chain, linear ketones having a substituent on the side chain, α-keto acids, and α-keto esters are preferred. Examples of cyclic ketones having a substituent on the side chain include cyclohexanone having a substituent at 2-position, cyclohexanone having a substituent at 3-position, cyclohexanone having a substituent at 4-position, cyclopentanone having a substituent at 2-position, cyclopentanone having a substituent at 3-position, azabicycloalkanone, adamantanone, cyclopentanone having substituents at 2- and 3-positions, cyclohexanone having substituents at 2- and 3-positions; more specifically, they include 2-methylcyclohexanone, 2-phenylcyclohexanone, ethyl 2-cyclohexanone carboxylate, 3-methylcyclohexanone, 4-phenylcyclohexanone, 4-tert-butylcyclohexanone, ethyl 4-cyclohexanone carboxylate, 1,4-cyclohexanedione, cyclopentanone-ethyl-2-carboxylate, 1-indanone, α-tetralone, 3-tetralone, 2-norbornanone, camphor, 8-azabicyclo[3.2.1]octane-3-one, tropinone, 3-quinuclidinone, 5-hydroxy-2-adamantanone, etc. Examples of linear ketones having a substituent on the side chain include phenyl acetone, (2-bromophenyl)acetone, 2-methoxyphenylacetone, 3-methoxyphenylacetone, 4-methoxyphenylacetone, 3,4-dimethoxyphenylacetone, 4-hydroxyphenylacetone, etc. Examples of α-keto acids include 3,3-dimethyl-2-oxobutyric acid, phenylpyruvic acid, 4-hydroxyphenylpyruvic acid, 4-hydroxy-3-methoxyphenylpyruvic acid, etc. Examples of α-keto esters include methyl pyruvate, methyl 2-oxopentanoate, methyl trifluoropyruvate, and methyl benzoylformate, etc.

Imine or enamine used in the reduction reaction of the present invention may be those generated simultaneously or those synthesized independently in a system, under the presence or absence of acid catalyst, using a carbonyl compound of general formula (6) and an amine compound of general formula (7) as raw materials.

As substituents, any various ones including substituent W may be present, and examples include, but are not limited to, hydrocarbon groups such as alkyl, alkenyl, cycloalkyl, cycloalkenyl, etc., fluoroalkyl group, halogen atom, oxygen-containing groups such as hydroxyl group, acyl group, alkoxy group, carboxyl group, ester group, etc., amino group, amide group, sulfonyl group, sulfenyl group, sulfo group, mercapto group, silyl group, nitro group, and cyano group, etc.

A ruthenium, rhodium, or iridium complex of general formula (1) which is used in the present invention may be prepared by mixing an organometallic compound of general formula (5):

[Formula 18]

$$(ArMQ_2)_p \quad (5)$$

(wherein p denotes an integer of 2 or more)
and a nitrogen-containing ligand of general formula (6):

[Formula 19]

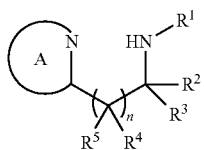

(6)

For example, a catalyst containing an organometallic complex of general formula (1) used in the present invention can be obtained as follows: under an inert gas atmosphere, an organometallic compound of general formula (5), a nitrogen-containing ligand of general formula (6) and a base are mixed in a halogen-based solvent, and the mixture is stirred at room temperature, then the resulting solution is washed with water, and dried under reduced pressure after distilling off the solvent.

Alternatively, it is possible to produce an amine compound as follows: under the presence of an organometallic compound of general formula (5), a nitrogen-containing ligand of general formula (6) and a base, one or more kinds selected from the group consisting of imine, iminium cation and enamine is reacted with hydrogen gas or a hydrogen-donating organic or inorganic compound.

The carbonyl compound is a compound, for example, represented by general formula (7):

[Formula 20]

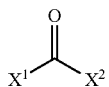

(7)

but is not limited thereto. In general formula (7), $X^1$ and $X^2$ are, independently of one another, a hydrogen atom, a hydroxyl group, a hydrocarbyl group, an aryl group in which a carbon atom may be replaced by a heteroatom, an alkylaryl group in which a carbon atom of the aryl may be replaced by a heteroatom, an aralkyl group in which a carbon atom of the aryl may be replaced by a heteroatom, a heterocyclyl group, a carboxyl group, an ester group, or an acyl group, wherein one or more hydrogen atoms of these groups may be substituted by any substituent. Examples of ester group include a group represented by —C(=O)—OR$^a$, and examples of acyl group include a group represented by —C(=O)—R$^a$.

Specific examples include, but are not limited to, alkyl groups such as methyl, ethyl, propyl, butyl, pentyl, hexyl, heptyl, etc., fluoroalkyl groups such as trifluoromethyl group, cycloalkyl groups such as cyclopropyl, cyclobutyl, cyclopentyl, cyclohexyl, etc., unsaturated hydrocarbons such as vinyl, allyl, etc., aromatic monocyclic or polycyclic groups such as phenyl, 1-naphthyl, 2-naphthyl, anthryl, phenanthryl, indenyl group, etc., heteromonocyclic or polycyclic groups such as thienyl, furyl, pyranyl, xanthenyl, pyridyl, pyrrolyl, imidazolinyl, indolyl, carbazolyl, phenanthrolinyl, etc., ester groups such as ferrocenyl group, carboxylic acid, methoxycarbonyl group, ethoxycarbonyl group, etc., acyl groups such as formyl group, acetyl group, benzoyl group, etc.

As substituents, any various ones including substituent W may be present, and examples include, but are not limited to, hydrocarbon groups such as alkyl, alkenyl, cycloalkyl, cycloalkenyl, etc., fluoroalkyl group, halogen atom, oxygen-containing groups such as hydroxyl group, acyl group, alkoxy group, carboxyl group, ester group, etc., amino group, amide group, sulfonyl group, sulfenyl group, sulfo group, mercapto group, silyl group, nitro group, and cyano group, etc.

$X^1$ and $X^2$ may be bonded to form a ring, and examples include, but are not limited to, a saturated or unsaturated cyclic hydrocarbon, a heteromonocyclic ring or polycyclic ring comprising heteroatoms such as nitrogen, oxygen, and sulfur atoms, etc., wherein one or more carbons of the ring may have a substituent, and preferred substituent includes a halogen atom, an oxygen-containing group such as alkoxy group, carboxyl group, and ester group, a nitro group, a cyano group, an alkyl group, preferably an alkyl group having carbon number of 1-20, an aryl group, an unsaturated alkyl group, a substituent having linear or cyclic hydrocarbon group containing a heteroatom. Specific examples include cycloalkanes such as cyclopentane ring, cyclohexane ring, and cycloheptane ring, which may have said substituent, 2,3-dihydro-1H-indene ring, or aryl-fused cycloalkanes such as 1,2,3,4-tetrahydronaphthalene ring, etc. which may have said substituent, and polycyclic alicyclic hydrocarbons such as decahydronaphthalene, etc.

In order to carry out the reaction at a higher diastereoselectivity, imines derived from cyclic ketones having a substituent on the side chain, linear ketones having a substituent on the side chain, α-keto acids, and α-keto esters are preferred. Examples of cyclic ketones having a substituent on the side chain include cyclohexanone having a substituent at 2-position, cyclohexanone having a substituent at 3-position, cyclohexanone having a substituent at 4-position, cyclopentanone having a substituent at 2-position, cyclopentanone having a substituent at 3-position, azabicycloalkanone, adamantanone, cyclopentanone having substituents at 2- and 3-positions, cyclohexanone having substituents at 2- and 3-positions; more specifically, they include 2-methylcyclohexanone, 2-phenylcyclohexanone, ethyl 2-cyclohexanone carboxylate, 3-methylcyclohexanone, 4-phenylcyclohexanone, 4-tert-butylcyclohexanone, ethyl 4-cyclohexanone carboxylate, 1,4-cyclohexanedione, cyclopentanone-ethyl-2-carboxylate, 1-indanone, α-tetralone, β-tetralone, 2-norbornanone, camphor, 8-azabicyclo[3.2.1]octane-3-one, tropinone, 3-quinuclidinone, 5-hydroxy-2-adamantanone, etc. Examples of linear ketones having a substituent on the side chain include phenyl acetone, (2-bromophenyl)acetone, 2-methoxyphenylacetone, 3-methoxyphenylacetone, 4-methoxyphenylacetone, 3,4-dimethoxyphenylacetone, 4-hydroxyphenylacetone, etc. Examples of α-keto acids include 3,3-dimethyl-2-oxobutyric acid, phenylpyruvic acid, 4-hydroxyphenylpyruvic acid, 4-hydroxy-3-methoxyphenylpyruvic acid, etc. Examples of α-keto esters include methyl pyruvate, methyl 2-oxopentanoate, methyl trifluoropyruvate, and methyl benzoylformate, etc.

When performing reductive amination reaction using the above-mentioned cyclic ketone having a substituent on the side chain, highly diastereoselective reaction proceeds to give corresponding cyclic amine. In addition, when performing reductive amination reaction using the above-mentioned linear ketone having a substituent on the side chain, α-keto acid, and α-keto ester as well as using optically active amine as the amine source, highly diastereoselective reaction proceeds to give amine or amino acid with high optical purity.

The amine compound as a raw material of the present invention is, for example, a compound of general formula (8):

[Formula 21]

$$NHY^1Y^2 \qquad (8)$$

but is not limited thereto. In general formula (8), $Y^1$ and $Y^2$ are a hydrogen atom, a hydroxyl group, a hydrocarbyl group, an aryl group in which a carbon atom may be replaced by a heteroatom, a heterocyclyl group, a sulfonyl group, an alkoxy group, an acyl group, an ester group, a carboxyl group, a phosphinyl group, a sulfinyl group or a silyl group, wherein one or more hydrogen atoms of these groups may be substituted by a substituent W.

Specific examples include, but are not limited to, alkyl groups such as methyl, ethyl, propyl, butyl, pentyl, hexyl, heptyl, etc., cycloalkyl groups such as cyclopropyl, cyclobutyl, cyclopentyl, cyclohexyl, etc., unsaturated hydrocarbons such as vinyl, allyl, etc., aromatic monocyclic or polycyclic groups such as phenyl, 1-naphthyl, 2-naphthyl, anthryl, phenanthryl, indenyl, etc., heteromonocyclic or polycyclic groups such as thienyl, furyl, pyranyl, xanthenyl, pyridyl, pyrrolyl, imidazolinyl, indolyl, carbazolyl, phenanthrolinyl, etc., and ferrocenyl group, etc.

Examples of the substituent may have various types such as a substituent W, and the substituent may be hydrocarbon groups such as alkyl, alkenyl, cycloalkyl, cycloalkenyl, etc., a fluoroalkyl group, a halogen atom, oxygen-containing groups such as hydroxyl group, acyl group, alkoxy group, carboxyl group, ester group, etc., an amino group, an amide group, a sulfonyl group, a sulfenyl group, a sulfo group, a mercapto group, a silyl group, a nitro group, and a cyano group, etc.

$Y^1$ and $Y^2$ may be bonded to form a ring, and in such a case, the examples include, but are not limited to, saturated and unsaturated alicyclic groups which give cyclic ketones such as pyrrolidine, piperidine, azepane, pyrrole, tetrahydropyridine, tetrahydroazepine, etc., and saturated and unsaturated alicyclic groups having a substituent having a linear or cyclic hydrocarbon group containing, at its respective carbon, an alkyl group, an aryl group, an unsaturated alkyl group and a heteroatom, etc. These amine compounds may be in the form of ammonium salt obtained by reaction with organic acid or inorganic acid. In particular, in order to synthesize primary amines, ammonium salts, benzylamine, racemic α-phenylethylamine, optically-active α-phenylethylamine are generally used.

From the viewpoint that synthetic intermediates of tamsulosin that is used in the treatment of dysuria in benign prostatic hyperplasia, or of formoterol that is used in the treatment of bronchial asthma, can be obtained with high yield and high diastereoselectivity, it is preferable to use, as a linear ketone, a phenyl acetone derivative that can be induced to tamsulosin or formoterol. As an amine compound to be reacted, it is preferable to use an optically active α-phenylethylamine in terms of easiness in availability of raw materials, production cost, reaction yield, and diastereoselectivity.

To carry out diastereoselective reaction, it is necessary for the carbonyl compound of general formula (7) and/or the amine compound of general formula (8) to have a chiral carbon; and an amine compound can be produced in a diastereoselective manner by appropriately combining these substrates.

In the present invention, in one aspect, one or more kinds selected from the group consisting of imine, iminium cation and enamine are optically active substances.

Furthermore, in one embodiment, one or more kinds selected from the group consisting of imine, iminium cation and enamine are optically active substances generated by the reaction of an optically active amine and a carbonyl compound.

Each of the imine, iminium cation, and enamine used in the present invention can also be easily obtained by condensation reaction of a carbonyl compound of general formula (7) and an amine compound of general formula (8), under the presence or absence of acid catalyst.

As the acid catalyst, it is desirable to add a Bronsted acid or a Lewis acid; examples of suitable Bronsted acid include organic acids such as carboxylic acid, sulfonic acid, phenols, etc., or mineral acids such as phosphoric acid, boric acid, hydrochloric acid, nitric acid, etc.; specifically, examples of acid catalyst include, but are not limited to, Bronsted acids such as formic acid, acetic acid, chloroacetic acid, trifluoroacetic acid, salicylic acid, p-toluenesulfonic acid, phenol, binaphthol, etc., or Lewis acids such as titanium tetraisopropoxide, aluminum triisopropoxide, etc. Also, optically active organic acids may be used, and as their specific examples, the following may be used: optically active carboxylic acids such as tartaric acid, mandelic acid, maleic acid, glutamic acid, camphorsulfonic acid, and derivatives thereof, amino acids such as alanine, arginine, asparagine, aspartic acid, cysteine, glutamine, glutamic acid, histidine, isoleucine, leucine, lysine, methionine, phenylalanine, proline, serine, threonine, tryptophan, tyrosine, valine, and derivatives thereof, or chiral phosphate compounds such as hydrogen phosphate-1,1'-binaphthyl-2,2'-diyl, and derivatives thereof. These may be used singly, or multiple kinds may be used in combination. In particular, since formic acid also acts as a hydrogen donor, it is a preferred Bronsead acid for the reductive amination reaction of carbonyl compound and amine compound. In generation of imines, iminium cations and/or enamines, since acidic conditions are preferred, it is also possible to use various buffers.

Hydrogen donors used in this specification refer to a compound capable of donating hydrogen by thermal effects, or by catalytic actions, and the kind of such hydrogen-donating compound is not particularly limited. Examples of suitable hydrogen donor compounds include methanol, ethanol, 1-propanol, 2-propanol, 1-butanol, sec-butyl alcohol, n-pentyl alcohol, cyclopentyl alcohol, n-hexyl alcohol, cyclohexyl alcohol, benzyl alcohol, formic acid, HCOOK, HCOONa, HCOONa, HCOOLi, HCOONH$_4$, etc.; and they may be used singly or in combination of plural kinds. In terms of reactivity and economic efficiency, preferable hydrogen donors are formic acid, formate, methanol, ethanol, and 2-propanol.

The amount of the hydrogen-donating compound used can be, relative to the carbonyl compound, from 1 to 30 equivalents; in terms of reactivity and economic efficiency, preferably 1 to 10 equivalents. When a formate such as HCOOK, HCOONa, HCOOLi, and HCOONH$_4$ are used as a hydrogen donor, the reaction may be carried out by addition of a phase transfer catalyst, if necessary. The phase transfer catalyst which may be used may be any salts having a long-chain alkyl ammonium cation; from the viewpoint of reactivity and economic efficiency, it is preferably tetrabutylammonium salt. By the addition of a phase transfer catalyst, in many cases, an effect of improving the reaction speed is observed. The amount of a phase transfer catalyst to be added is generally in the range of 0.001 to 10 molar equivalents relative to the carbonyl compound; from the viewpoint of reactivity and economic efficiency, it is preferably 0.01 to 0.1 molar equivalents.

The amount of the amine compound used can be, relative to the carbonyl compound, generally from 1 to 30 equivalents; in terms of reactivity and economic efficiency, preferably 1 to 10 equivalents. When a gas such as ammonia is used as the amine compound, it can be used directly as a gas or used by being dissolved in aqueous ammonia or a solvent, etc., or it can be used as an ammonium salt.

The ammonium salt which may be used may be any salt containing ammonia, and examples include ammonium formate, ammonium acetate, ammonium chloride, ammonium bromide, ammonium fluoride, ammonium iodide, ammonium phosphate, ammonium hexafluorophosphate, ammonium thiocyanate, ammonium benzoate, ammonium hydroxide, ammonium perchlorate, ammonium sulfate, ammonium nitrate, ammonium carbonate, ammonium bicarbonate, etc.; from the viewpoint of reactivity and economic efficiency, it is preferably ammonium formate, ammonium acetate or ammonium chloride.

Regarding the amount of a catalyst comprising an organometallic complex of general formula (1), the molar ratio of the carbonyl compound to the ruthenium, rhodium or iridium catalyst may be expressed as S/C (S represents the number of moles of carbonyl compound, imine or enamine, and C represents the number of moles of the catalyst). In this case, a possible maximum value of S/C significantly varies depending on the structure of substrate, the type and concentration of catalyst, reaction temperature and the type of hydrogen donor; practically, it is desirable to set S/C=100 to approximately 20000.

In the present invention, a reaction solvent may be appropriately used, with consideration given to physical properties and chemical properties of carbonyl compound, amine compound, imine, iminium cation, enamine, acid, hydrogen gas and hydrogen-donating compound. Protic solvents, aprotic solvents, ionic liquids, water and buffers may be used singly or in combination of plural kinds.

Reaction temperature may be, considering the solubility and reactivity of substrate and product as well as economic efficiency, set at preferably from −20° C. to approximately 100° C., and more preferably from 20° C. to 80° C. Reaction time varies depending on the reaction conditions such as substrate concentration, temperature and pressure, etc., however, the reaction will complete within a few minutes to 100 hours.

Purification of the resulting amine compound can be carried out by a known method such as acid-base extraction, column chromatography, distillation, recrystallization or an appropriate combination thereof.

In the present invention, it is possible to produce an amine compound as follows: under the presence of an organometallic compound of general formula (5), a nitrogen-containing ligand of general formula (6) and a base, by reacting a carbonyl compound, an amine compound, and hydrogen gas or a hydrogen-donating organic or inorganic compound, or by reacting one or more kinds selected from the group consisting of imine, iminium cation and enamine with hydrogen gas or a hydrogen-donating organic or inorganic compound.

EXAMPLES

The present invention is described in more detail with reference to the following examples; however, the invention is not limited to these examples.

The reactions described in the Production Examples and Reaction Examples below were carried out under an inert gas atmosphere of argon gas or nitrogen gas. Regarding carbonyl compounds and amine compounds used, commercially available reagents were used without modification. For the identification of ligand complexes and reaction products, a nuclear magnetic resonance apparatus (NMR) was used, wherein tetramethylsilane (TMS) was the internal standard substance and its signal was set as $\delta=0$ ($\delta$: chemical shift). The conversion rate into amine compound and the reaction yield of amine compound were determined by measurement of crude product using gas chromatography (GC) and NMR, and by calculation using each of the integral values of raw materials, target product, and by-products.

The conversion rate into amine compound was calculated by [(Sum of the integral values of target product and by-products)/(Sum of each of the integral values of raw materials, target product and by-products)]×100, the reaction yield of amine compound was calculated by [(Integral value of target product)/(Sum of each of the integral values of raw materials, target product and by-products)]×100. An isolation yield refers to the yield of a reaction product actually isolated, and is calculated by (mole number of isolated reaction product/mole number of starting compound)×100. JNM-ECX-400P (JEOL, Ltd.) was used as NMR apparatus, GC-17A (Shimadzu Corporation) was used as GC device, and capillary column TC-1 (GL Sciences Inc.) (length 30 m, inner diameter 0.32 mm, film thickness 0.25 μm) was used as separation column, CHIRALCEL OD-H (Daicel Corporation) (0.46 cm×25 cm) was used as HPLC chiral column. For optical rotation measurement, P-2200 (JASCO Corporation) was used. FIG. 1 shows complexes which are one embodiment of the organometallic compound of the present invention, used in the Reaction Examples.

Synthesis of Iridium Complex

Production Example 1

Synthesis of Cp*IrCl((S)—N-(1-(pyridin-2-yl)ethyl)methanesulfonamide) complex ((S)-Complex 1)

In a 20-mL Schlenk, [Cp*IrCl$_2$]$_2$ (MW: 796.67) (831 mg, 1.04 mmol) and (S)—N-(1-(pyridin-2-yl)ethyl)methanesulfonamide (MW: 200.26) (418 mg, 2.09 mmol) were charged, and replaced with argon gas. Dehydrated methylene chloride (12 mL) and triethylamine (MW: 101.19) (289 μL, 2.09 mmol) were added thereto, and the mixture was stirred at room temperature for 15 h. The mixture was washed with a small amount of water for 3 times, the organic solvent was distilled off, then the mixture was dried under reduced pressure, suspended and washed in MTBE (20 mL), and dried in vacuo to afford yellow powder crystals (966 mg, 83% yield).

$^1$H NMR (400 MHz, CDCl$_3$, $\delta$/ppm): 1.44 (d, J=6.9 Hz, 3H), 1.67 (s, 15H), 2.96 (s, 3H), 5.10 (q, J=6.9 Hz, 1H), 7.23 (m, 1H), 7.34 (d, J=7.8 Hz, 1H), 7.76 (td, J=7.8, 1.4 Hz, 1H), 8.49 (d, J=5.0 Hz, 1H).

$^{13}$C NMR (100 MHz, CDCl$_3$, δ/ppm): 9.3, 26.8, 43.4, 64.7, 87.0, 120.6, 124.5, 138.4, 151.2, 169.8.

Production Example 2

Synthesis of Cp*IrCl((S)—N-(phenyl(pyridin-2-yl)methyl)methanesulfonamide) complex ((S)-Complex 2)

In a 20-mL Schlenk, [Cp*IrCl$_2$]$_2$ (MW: 796.67) (397 mg, 0.502 mmol) and (S)—N-(phenyl(pyridin-2-yl)methyl)methanesulfonamide (MW: 262.33) (277 mg, 1.06 mmol) were charged, and replaced with argon gas. Dehydrated methylene chloride (5 mL) and triethylamine (MW: 101.19) (140 μL, 1.00 mmol) were added thereto, and the mixture was stirred at room temperature for 19 h. The mixture was washed with a small amount of water for 4 times, the organic solvent was distilled off, then the mixture was dried under reduced pressure, suspended and washed in IPE (20 mL), and dried in vacuo to afford orange powder crystals (527 mg, 80% yield).
$^1$H NMR (400 MHz, CDCl$_3$, δ/ppm): 1.37 (s, 15H), 3.02 (s, 3H), 6.08 (s, 1H), 7.22-7.30 (m, 3H), 7.32-7.40 (m, 3H), 7.50 (d, J=7.8 Hz, 1H), 7.85 (dt, J=7.8, 0.9 Hz, 1H), 8.61 (dd, J=5.0, 0.9 Hz, 1H).
$^{13}$C NMR (100 MHz, CDCl$_3$, δ/ppm): 8.8, 44.8, 70.6, 87.1, 122.4, 125.0, 127.5, 128.1, 128.3, 138.1, 143.9, 152.6, 165.7.

Production Example 3

Synthesis of Cp*IrCl(N-(phenyl(pyridin-2-yl)methyl)methanesulfonamide) complex (Complex 3)

In a 20-mL Schlenk, [Cp*IrCl$_2$]$_2$ (MW: 796.67) (200 mg, 0.251 mmol) and N-(phenyl(pyridin-2-yl)methyl)methanesulfonamide (MW: 262.33) (166 mg, 0.632 mmol) were charged, and replaced with argon gas. Dehydrated methylene chloride (5 mL) and triethylamine (MW: 101.19) (73 μL, 0.527 mmol) were added thereto, and the mixture was stirred at room temperature for 14 h. The mixture was washed with a small amount of water for 4 times, the organic solvent was distilled off, then the mixture was dried under reduced pressure, suspended and washed in IPE (20 mL), and dried in vacuo to afford orange powder crystals (290 mg, 93% yield).
$^1$H NMR (400 MHz, CDCl$_3$, δ/ppm): 1.37 (s, 15H), 3.02 (s, 3H), 6.08 (s, 1H), 7.22-7.30 (m, 3H), 7.32-7.40 (m, 3H), 7.50 (d, J=7.8 Hz, 1H), 7.85 (dt, J=7.8, 0.9 Hz, 1H), 8.61 (dd, J=5.0, 0.9 Hz, 1H).
$^{13}$C NMR (100 MHz, CDCl$_3$, δ/ppm): 8.8, 44.8, 70.6, 87.1, 122.4, 125.0, 127.5, 128.1, 128.3, 138.1, 143.9, 152.6, 165.7.

Production Example 4

Synthesis of Cp*IrCl(N-(1-(pyridin-2-yl)ethyl)methanesulfonamide) complex (Complex 4)

In a 20-mL Schlenk, [Cp*IrCl$_2$]$_2$ (MW: 796.67) (200 mg, 0.251 mmol) was charged, and replaced with argon gas. Dehydrated methylene chloride (6 mL), N-(1-(pyridin-2-yl)ethyl)methanesulfonamide (MW: 200.26) (106 mg, 0.527 mmol) and triethylamine (MW: 101.19) (73 μL, 0.527 mmol) were added thereto, and the mixture was stirred at room temperature for 18 h. The mixture was washed with a small amount of water for 3 times, the organic solvent was distilled off, then the mixture was dried under reduced pressure. After it was suspended and washed by addition of MTBE (20 mL), crystals were collected by filtering, and dried under reduced pressure to afford yellow powder crystals (237 mg, 84% yield).
$^1$H NMR (400 MHz, CDCl$_3$, δ/ppm): 1.44 (d, J=6.9 Hz, 3H), 1.67 (s, 15H), 2.96 (s, 3H), 5.10 (q, J=6.9 Hz, 1H), 7.23 (m, 1H), 7.34 (d, J=7.8 Hz, 1H), 7.76 (td, J=7.8, 1.4 Hz, 1H), 8.49 (d, J=5.0 Hz, 1H).
$^{13}$C NMR (100 MHz, CDCl$_3$, δ/ppm): 9.3, 26.8, 43.4, 64.7, 87.0, 120.6, 124.5, 138.4, 151.2, 169.8.

Production Example 5

Synthesis of Cp*IrCl(4-methyl-N-(1-(pyridin-2-yl)ethyl)benzenesulfonamide) complex (Complex 5)

In a 20-mL Schlenk, [Cp*IrCl$_2$]$_2$ (MW: 796.67) (200 mg, 0.251 mmol) was charged, and replaced with argon gas. Dehydrated methylene chloride (6 mL), 4-methyl-N-(1-(pyridin-2-yl)ethyl)benzenesulfonamide (MW: 276.35) (146 mg, 0.527 mmol) and triethylamine (MW: 101.19) (73 μL, 0.527 mmol) were added thereto, and the mixture was stirred at room temperature for 15 h. The mixture was washed with a small amount of water for 3 times, the organic solvent was distilled off, then the mixture was dried under reduced pressure. After it was suspended and washed by addition of IPE (20 mL), crystals were collected by filtering, and dried under reduced pressure to afford yellow powder crystals (297 mg, 88% yield).
$^1$H NMR (400 MHz, CDCl$_3$, δ/ppm): 1.37 (s, 15H), 3.02 (s, 3H), 6.08 (s, 1H), 7.26 (m, 3H), 7.34 (m, 3H), 7.50 (d, J=7.8 Hz, 1H), 7.85 (dt, J=7.8, 0.9 Hz, 1H), 8.61 (dd, J=5.0, 0.9 Hz, 1H).
$^{13}$C NMR (100 MHz, CDCl$_3$, δ/ppm): 9.3, 26.4, 63.2, 65.5, 86.9, 120.6, 124.2, 126.7, 127.8, 130.9, 133.3, 137.7, 150.8, 169.8.

Production Example 6

Synthesis of Cp*IrCl(1-phenyl-N-(1-(pyridin-2-yl)ethyl)methanesulfonamide) complex (Complex 6)

In a 20-mL Schlenk, [Cp*IrCl$_2$]$_2$ (MW: 796.67) (200 mg, 0.251 mmol) was charged, and replaced with argon gas. Dehydrated methylene chloride (6 mL), 1-phenyl-N-(1-(pyridin-2-yl)ethyl)methanesulfonamide (MW: 276.35) (146 mg, 0.527 mmol) and triethylamine (MW: 101.19) (73 μL, 0.527 mmol) were added thereto, and the mixture was stirred at room temperature for 15 h. The mixture was washed with a small amount of water for 3 times, the organic solvent was distilled off, then the mixture was dried under reduced pressure. After it was suspended and washed by addition of IPE (20 mL), crystals were collected by filtering, and dried under reduced pressure to afford yellow powder crystals (287 mg, 85% yield).
$^1$H NMR (400 MHz, CDCl$_3$, δ/ppm): 1.19 (d, J=6.9 Hz, 3H), 1.66 (s, 15H), 4.34 (q, J=6.9 Hz, 1H), 4.44 (d, J=12.8 Hz, 1H), 4.64 (d, J=12.8 Hz, 1H), 6.77 (d, J=7.8 Hz, 1H), 6.99 (dd, J=7.8, 7.3 Hz, 2H), 7.12 (dd, J=7.8, 6.9 Hz, 1H), 7.22 (dd, J=6.9, 5.5 Hz, 1H), 7.38 (d, J=7.8 Hz, 2H), 7.65 (dd, J=7.8, 7.3 Hz, 1H), 8.50 (d, J=5.5 Hz, 1H).
$^{13}$C NMR (100 MHz, CDCl$_3$, δ/ppm): 9.3, 26.4, 63.2, 65.5, 86.9, 120.6, 124.2, 126.7, 127.8, 130.9, 133.3, 137.7, 150.8, 169.8.

Production Example 7

Synthesis of Cp*RhCl(N-(1-(pyridin-2-yl)ethyl)methanesulfonamide) complex (Complex 7)

In a 20-mL Schlenk, [Cp*RhCl$_2$]$_2$ (MW: 618.08) (100 mg, 0.162 mmol) was charged, and replaced with argon gas. Dehydrated methylene chloride (4 mL), N-(1-(pyridin-2-yl)ethyl)methanesulfonamide (MW: 200.26) (65 mg, 0.324 mmol) and triethylamine (MW: 101.19) (45 μL, 0.324 mmol) were added thereto, and the mixture was stirred at room temperature for 20 h. The mixture was washed with a small amount of water for 2 times, the organic solvent was distilled off, then the mixture was dried under reduced pressure. After it was suspended and washed by addition of IPE (20 mL), crystals were collected by filtering, and dried under reduced pressure to afford yellow powder crystals (122 mg, 80% yield).

$^1$H NMR (400 MHz, CDCl$_3$, δ/ppm): 1.54 (d, J=6.4 Hz, 3H), 1.70 (s, 15H), 2.86 (s, 3H), 4.77 (q, J=6.4 Hz, 1H), 7.20-7.35 (m, 2H), 7.75 (td, J=7.8, 1.4 Hz, 1H), 8.50 (d, J=5.5 Hz, 1H).

$^{13}$C NMR (100 MHz, CDCl$_3$, δ/ppm): 9.5, 27.3, 41.2, 63.8, 95.0, 95.1, 121.2, 124.0, 138.2, 150.9, 169.5.

Production Example 8

Synthesis of Cp*IrCl(N-(1-(thiazol-2-yl)ethyl)methanesulfonamide) complex (Complex 8)

In a 20-mL Schlenk, [Cp*IrCl$_2$]$_2$ (MW: 796.67) (224 mg, 0.284 mmol) and N-(1-(thiazol-2-yl)ethyl)methanesulfonamide (MW: 206.26) (123 mg, 0.597 mmol) were charged, and replaced with argon gas. Dehydrated methylene chloride (5 mL) and triethylamine (MW: 101.19) (80 μL, 0.568 mmol) were added thereto, and the mixture was stirred at room temperature for 17 h. The mixture was washed with a small amount of water for 4 times, the organic solvent was distilled off, then the mixture was dried under reduced pressure, suspended and washed in IPE (20 mL), and dried in vacuo to afford orange powder crystals (237 mg, 70% yield).

$^1$H NMR (400 MHz, CDCl$_3$, δ/ppm): 1.50 (d, J=6.4 Hz, 1H), 1.69 (s, 15H), 2.98 (s, 3H), 5.15 (q, J=6.4 Hz, 1H), 7.48 (d, J=3.7 Hz, 1H), 7.59 (d, J=3.7 Hz, 1H).

$^{13}$C NMR (100 MHz, CDCl$_3$, δ/ppm): 9.3, 27.9, 43.0, 60.6, 86.6, 121.9, 139.7, 179.3.

Production Example 9

Synthesis of Cp*IrCl((S)—N-(phenyl(pyridin-2-yl)methyl)acetamide) complex ((S)-Complex 9)

In a 20-mL Schlenk, [Cp*IrCl$_2$]$_2$ (MW: 796.67) (100 mg, 0.126 mmol) and (S)—N-(phenyl(pyridin-2-yl)methyl)acetamide (MW: 164.20) (46 mg, 0.277 mmol) were charged, and replaced with argon gas. Dehydrated methylene chloride (5 mL) and triethylamine (MW: 101.19) (37 μL, 0.277 mmol) were added thereto, and the mixture was stirred at room temperature for 19 h. The mixture was washed with a small amount of water for 4 times, the organic solvent was distilled off, then the mixture was dried under reduced pressure, suspended and washed in IPE (20 mL), and dried in vacuo to afford orange powder crystals (54 mg, 41% yield).

$^1$H NMR (400 MHz, CDCl$_3$, δ/ppm): 1.37 (d, J=6.9 Hz, 1H), 1.64 (s, 15H), 2.30 (s, 3H), 6.06 (q, J=6.9, Hz, 1H), 7.21 (t, J=6.4, 1H), 7.36 (d, J=7.8 Hz, 1H), 7.73 (t, J=7.3, 1H), 8.41 (d, J=5.5 Hz, 1H).

$^{13}$C NMR (100 MHz, CDCl$_3$, δ/ppm): 9.3, 22.3, 26.0, 63.9, 86.4, 120.6, 124.2, 138.3, 150.9, 170.2, 175.0.

Production Example 10

Synthesis of Cp*IrCl((S)-1-phenyl-3-(1-(pyridin-2-yl)ethyl)urea) complex ((S)-Complex 10)

In a 20-mL Schlenk, [Cp*IrCl$_2$]$_2$ (MW: 796.67) (100 mg, 0.126 mmol) and (S)-1-phenyl-3-(1-(pyridin-2-yl)ethyl)urea (MW: 241.29) (64 mg, 0.265 mmol) were charged, and replaced with argon gas. Dehydrated methylene chloride (5 mL) and triethylamine (MW: 101.19) (37 μL, 0.277 mmol) were added thereto, and the mixture was stirred at room temperature for 14 h. The mixture was washed with a small amount of water for 4 times, the organic solvent was distilled off, then the mixture was dried under reduced pressure, suspended and washed in IPE (20 mL), and dried in vacuo to afford orange powder crystals (116 mg, 76% yield).

$^1$H NMR (400 MHz, CDCl$_3$, δ/ppm): 1.45 (d, J=6.9 Hz, 1H), 1.66 (s, 15H), 5.80 (q, J=6.9 Hz, 1H), 6.82 (t, J=7.3 Hz, 1H), 7.16-7.24 (m, 3H), 7.32-7.36 (m, 2H), 7.38 (d, J=7.8 Hz, 1H), 7.60 (s, 1H), 7.74 (td, J=7.8, 1.4 Hz, 1H), 8.47 (d, J=5.0 Hz, 1H).

$^{13}$C NMR (100 MHz, CDCl$_3$, δ/ppm): 9.2, 23.7, 64.4, 86.8, 117.9, 119.7, 120.7, 124.2, 128.4, 138.3, 142.4, 151.0, 160.1, 170.9.

Production Example 11

Synthesis of Cp*IrCl(N-(1-(isoquinolin-1-yl)naphthalen-2-yl)acetamide) complex (Complex 11)

In a 20-mL Schlenk, [Cp*IrCl$_2$]$_2$ (MW: 796.67) (150 mg, 0.188 mmol) was charged, and replaced with argon gas. Dehydrated methylene chloride (4 mL), N-(1-(isoquinolin-1-yl)naphthalen-2-yl)acetamide (MW: 312.36) (124 mg, 0.395 mmol), and triethylamine (MW: 101.19) (55 μL, 0.395 mmol) were added thereto, and the mixture was stirred at room temperature for 24 h. The mixture was washed with a small amount of water for 3 times, the organic solvent was distilled off, then the mixture was dried under reduced pressure. After it was suspended and washed by addition of IPE (20 mL), crystals were collected by filtering, and dried under reduced pressure to afford yellow powder crystals (253 mg, 99% yield).

$^1$H NMR (400 MHz, CDCl$_3$, δ/ppm): 1.31 (s, 15H), 2.42 (s, 3H), 6.69 (d, J=8.2 Hz, 1H), 7.05 (td, J=8.7, 1.4 Hz, 1H), 7.20-7.32 (m, 3H), 7.49 (d, J=8.7 Hz, 1H), 7.60-7.72 (m, 2H), 7.79 (d, J=7.8 Hz, 1H), 7.81-7.91 (m, 2H), 8.05 (d, J=8.7 Hz, 1H), 8.85 (d, J=6.4 Hz, 1H).

$^{13}$C NMR (100 MHz, CDCl$_3$, δ/ppm): 8.5, 26.4, 26.5, 86.1, 121.5, 123.8, 124.4, 125.8, 125.9, 126.2, 126.5, 127.8, 128.0, 128.2, 129.3, 129.8, 131.2, 131.9, 133.4, 136.4, 145.9, 153.5, 157.0, 177.9.

<Reductive Amination Reaction>

FIGS. 2-7 show reaction formulae of the Reaction Examples below. The following reactions were all carried out under acidic conditions. In said reaction formulae, when the complexes synthesized by the above-mentioned production method are used as a catalyst, said complexes are described as "catalyst" with the corresponding number. Namely, for example in the following reaction formula, when the complex 1 is used as the catalyst, the complex 1 is described as catalyst 1. In addition, because the complexes synthesized by the above production method have both the optically active form and racemate, in the following Reaction Examples, the absolute configuration ((S) or (R)) is described before the notation "catalyst" when using optically active complexes, and when using racemic complexes, absolute configuration is not described.

Reaction Example 1

Synthesis of (R)-1-(2-methoxyphenyl)-N—((R)-1-phenylethyl)propan-2-amine

In a 20-mL Schlenk, (S)-catalyst 1 (MW: 562.15) (1.12 mg, 0.002 mmol, S/C=500) was charged, then dried under reduced pressure and replaced with argon gas. Methanol (1 mL), 1-(2-methoxyphenyl)propan-2-one (MW: 164.20) (153 μL, 1.0 mmol), (R)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 16 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (97% yield). The resulting compound was deprotected with Pd—C and acetylated, and the optical purity and optical rotation of the obtained acetyl amide compound were measured as follows: optical purity: 97% ee, optical rotation: $[\alpha]_D^{30}$=+22.2 (c=1.05, CHCl$_3$).

Reaction Example 2

Synthesis of (R)-1-(4-methoxyphenyl)-N—((R)-1-phenylethyl)propan-2-amine

In a 20-mL Schlenk, (S)-catalyst 1 (MW: 562.15) (1.12 mg, 0.002 mmol, S/C=500) was charged, then dried under reduced pressure and replaced with argon gas. Methanol (1 mL), 1-(2-methoxyphenyl)propan-2-one (MW: 164.20) (153 μL, 1.0 mmol), (R)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 16 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (89% yield). The resulting compound was deprotected with Pd—C and acetylated, and the optical purity and optical rotation of the obtained acetyl amide compound were measured as follows: optical purity: 88% ee, optical rotation: $[\alpha]_D^{30}$=+35.9 (c=0.95, CHCl$_3$).

Reaction Example 3

Synthesis of (R)-1-(4-methoxyphenyl)-N—((R)-1-phenylethyl)propan-2-amine

In a 20-mL Schlenk, (S)-catalyst 2 (MW: 624.22) (1.25 mg, 0.002 mmol, S/C=500) was charged, then dried under reduced pressure and replaced with argon gas. Methanol (1 mL), 1-(2-methoxyphenyl)propan-2-one (MW: 164.20) (153 μL, 1.0 mmol), (R)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 14 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (88% yield). The resulting compound was deprotected with Pd—C and acetylated, and the optical purity and optical rotation of the obtained acetyl amide compound were measured as follows: optical purity: 80% ee, optical rotation: $[\alpha]_D^{30}$=+30.9 (c=0.95, CHCl$_3$).

Reaction Example 4

Synthesis of (S)-1-(4-methoxyphenyl)-N—((S)-1-phenylethyl)propan-2-amine

In a 20-mL Schlenk, (S)-catalyst 2 (MW: 624.22) (1.25 mg, 0.002 mmol, S/C=500) was charged, then dried under reduced pressure and replaced with argon gas. Methanol (1 mL), 1-(2-methoxyphenyl)propan-2-one (MW: 164.20) (153 μL, 1.0 mmol), (S)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 22 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (89% yield). The resulting compound was deprotected with Pd—C and acetylated, and the optical purity and optical rotation of the obtained acetyl amide compound were measured as follows: optical purity: 85% ee, optical rotation: $[\alpha]_D^{30}$=−33.2 (c=0.95, CHCl$_3$).

Reaction Example 5

Synthesis of (R)-1-(4-methoxyphenyl)propan-2-amine

In a 20-mL Schlenk, (S)-catalyst 1 (MW: 562.15) (1.12 mg, 0.002 mmol, S/C=500) was charged, then dried under reduced pressure and replaced with argon gas. Methanol (1 mL), 1-(2-methoxyphenyl)propan-2-one (MW: 164.20) (153 μL, 1.0 mmol), ammonium formate (MW: 63.06) (189 mg, 3 mmol), and acetic acid (MW: 60.05) (57 μL, 1.0 mmol) were added thereto, and the mixture was stirred with heating at 60° C. for 4 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (89% yield). The resulting compound was acetylated, and the optical purity and optical rotation of the obtained acetyl amide compound were measured as follows: optical purity: 7% ee, optical rotation: $[\alpha]_D^{30}$, =+2.1 (c=0.95, CHCl$_3$).

Reaction Example 6

Synthesis of (R)—N-benzyl-1-(4-methoxyphenyl)propan-2-amine

In a 20-mL Schlenk, (S)-catalyst 1 (MW: 562.15) (1.12 mg, 0.002 mmol, S/C=500) was charged, then dried under reduced pressure and replaced with argon gas. Methanol (1 mL), 1-(2-methoxyphenyl)propan-2-one (MW: 164.20) (153 μL, 1.0 mmol), benzyl amine (MW: 107.15) (120 μL, 1.1 mmol), and formic acid (MW: 46.03) (113 μL, 3.0 mmol) were added thereto, and the mixture was stirred with heating at 40° C. for 18 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (100% yield). The resulting compound was deprotected with Pd—C and acetylated, and the optical purity and optical rotation of the obtained acetyl amide compound were measured as follows: optical purity: 13% ee, optical rotation: $[\alpha]_D^{30}$ =+5.6 (c=0.95, CHCl$_3$).

Reaction Example 7

Synthesis of N—((R)-1-phenylethyl)-1,2,3,4-tetrahydronaphthalen-2-amine

In a 20-mL Schlenk, (S)-catalyst 1 (MW: 562.15) (1.12 mg, 0.002 mmol, S/C=500) was charged, then dried under reduced pressure and replaced with argon gas. Methanol (1 mL), β-tetralone (MW: 146.19) (133 μL, 1.0 mmol), (R)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 23 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (97% yield). Diastereoselectivity of the obtained compound was 40% de.

Reaction Example 8

Synthesis of N—((S)-1-phenylethyl)-1,2,3,4-tetrahydronaphthalen-2-amine

In a 20-mL Schlenk, (S)-catalyst 1 (MW: 562.15) (1.12 mg, 0.002 mmol, S/C=500) was charged, then dried under reduced pressure and replaced with argon gas. Methanol (1 mL), β-tetralone (MW: 146.19) (133 μL, 1.0 mmol), (S)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 23 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (94% yield). Diastereoselectivity of the obtained compound was 27% de.

Reaction Example 9

Synthesis of N—((R)-1-phenylethyl)-1,2,3,4-tetrahydronaphthalen-2-amine

In a 20-mL Schlenk, (S)-catalyst 2 (MW: 624.22) (1.25 mg, 0.002 mmol, S/C=500) was charged, then dried under reduced pressure and replaced with argon gas. Methanol (1 mL), β-tetralone (MW: 146.19) (133 μL, 1.0 mmol), (R)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 20 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (84% yield). Diastereoselectivity of the obtained compound was 18% de.

Reaction Example 10

Synthesis of N—((S)-1-phenylethyl)-1,2,3,4-tetrahydronaphthalen-2-amine

In a 20-mL Schlenk, (S)-catalyst 2 (MW: 624.22) (1.25 mg, 0.002 mmol, S/C=500) was charged, then dried under reduced pressure and replaced with argon gas. Methanol (1 mL), β-tetralone (MW: 146.19) (133 μL, 1.0 mmol), (S)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 20 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (98% yield). Diastereoselectivity of the obtained compound was 28% de.

Reaction Example 11

Synthesis of (R)-1-phenyl-N—((R)-1-(pyridin-2-yl)ethyl)ethanamine

In a 20-mL Schlenk, (S)-catalyst 1 (MW: 562.15) (1.12 mg, 0.002 mmol, S/C=500) was charged, then dried under reduced pressure and replaced with argon gas. Methanol (1 mL), 2-acetylpyridine (MW: 121.14) (112 μL, 1.0 mmol), (R)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 14 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR

Reaction Example 12

Synthesis of 1-(4-nitrophenyl)ethanamine

In a 20-mL Schlenk, catalyst 3 (MW: 624.22) (6.24 mg, 0.010 mmol, S/C=500) was charged, then dried under reduced pressure and replaced with argon gas. Methanol (5 mL), 1-(4-nitrophenyl)ethanone (MW: 165.15) (826 mg, 5.0 mmol), ammonium formate (MW: 63.06) (946 mg, 15 mmol), and acetic acid (MW: 60.05) (286 μL, 5.0 mmol) were added thereto, and the mixture was stirred with heating at 60° C. for 4 h. The solvent was concentrated under reduced pressure, 1 M KOH (25 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (90% yield).

Reaction Example 13

Synthesis of 4-(1-aminoethyl)benzonitrile

In a 20-mL Schlenk, catalyst 3 (MW: 624.22) (6.24 mg, 0.010 mmol, S/C=500) was charged, then dried under reduced pressure and replaced with argon gas. Methanol (5 mL), 4-acetyl benzonitrile (MW: 145.16) (726 mg, 5.0 mmol), ammonium formate (MW: 63.06) (946 mg, 15 mmol), and acetic acid (MW: 60.05) (286 μL, 5.0 mmol) were added thereto, and the mixture was stirred with heating at 60° C. for 4 h. The solvent was concentrated under reduced pressure, 1 M KOH (25 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by H-NMR was carried out using coumarin as the internal standard substance (91% yield).

Reaction Example 14

Synthesis of cis-4-methylcyclohexylamine

In a 20-mL Schlenk, ammonium formate (MW: 63.06) (946 mg, 15.0 mmol) was charged, and replaced with argon gas. Dehydrated methanol (5 mL), 4-methylcyclohexanone (MW: 112.17) (614 μL, 5.0 mmol), acetic acid (286 μL, 5.0 mmol), and catalyst 3 (MW: 624.22) (6.24 mg, 0.01 mmol, S/C=500) were added thereto, and the mixture was stirred with heating at 60° C. for 4 h. After distilling off the solvent, 1 M KOH solution (20 mL) was added, and the mixture was extracted with dichloromethane (40 mL). The organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance. The yield of the obtained cis-4-methylcyclohexylamine was 70%. The compound obtained showed cis:trans=91:9 by GC analysis.

Reaction Example 15

Synthesis of cis-4-(tert-butyl)cyclohexylamine

In a 20-mL Schlenk, ammonium formate (MW: 63.06) (946 mg, 15.0 mmol) was charged, and replaced with argon gas. Dehydrated methanol (5 mL), 4-tert-butylcyclohexanone (MW: 154.25) (771 mg, 5.0 mmol), acetic acid (286 μL, 5.0 mmol), and catalyst 3 (MW: 624.22) (6.24 mg, 0.01 mmol, S/C=500) were added thereto, and the mixture was stirred with heating at 60° C. for 4 h. After distilling off the solvent, 1 M KOH solution (25 mL) was added, and the mixture was extracted with dichloromethane (40 mL). The organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance. The yield of the obtained cis-4-(tert-butyl)cyclohexylamine was 71%. The compound obtained showed cis:trans=99.1:0.9 by GC analysis.

Reaction Example 16

Synthesis of cis-4-(tert-butyl)cyclohexylamine

In a 20-mL Schlenk, ammonium formate (MW: 63.06) (189 mg, 3.0 mmol) was charged, and replaced with argon gas. Dehydrated methanol (1 mL), 4-tert-butylcyclohexanone (MW: 154.25) (154 mg, 1.0 mmol), acetic acid (57 μL, 1.0 mmol), and (S)-catalyst 9 (MW: 568.17) (2.84 mg, 0.005 mmol, S/C=200) were added thereto, and the mixture was stirred with heating at 60° C. for 4 h. After distilling off the solvent, 1 M KOH solution (10 mL) was added, and the mixture was extracted with dichloromethane (40 mL). The organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance. The yield of the obtained cis-4-(tert-butyl)cyclohexylamine was 71%. The compound obtained showed cis:trans=99.1:0.9 by GC analysis.

Reaction Example 17

Synthesis of cis-4-phenylcyclohexylamine

In a 20-mL Schlenk, ammonium formate (MW: 63.06) (946 mg, 15.0 mmol) was charged, and replaced with argon gas. Dehydrated methanol (5 mL), 4-phenylcyclohexanone (MW: 174.27) (871 mg, 5.0 mmol), acetic acid (286 μL, 5.0 mmol), and catalyst 3 (MW: 624.22) (6.24 mg, 0.01 mmol, S/C=500) were added thereto, and the mixture was stirred with heating at 60° C. for 7 h. After distilling off the solvent, 1 M KOH (20 mL) was added, and the mixture was extracted with dichloromethane (40 mL). The organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance. The yield of the obtained cis-4-phenylcyclohexylamine was 97%. The compound obtained showed cis:trans=95.2:4.8 by GC analysis.

Reaction Example 18

Synthesis of 1-phenylethylamine

In a 20-mL Schlenk, ammonium formate (MW: 63.06) (946 mg, 15.0 mmol) was charged, and replaced with argon

--- was carried out using coumarin as the internal standard substance (98% yield). Diastereoselectivity of the obtained compound was 88% de.

gas. Dehydrated methanol (5 mL), acetophenone (MW: 120.15) (582 µL, 5.0 mmol), acetic acid (286 µL, 5.0 mmol), and (S)-catalyst 1 (MW: 562.15) (5.62 mg, 0.01 mmol, S/C=500) were added thereto, and the mixture was stirred with heating at 60° C. for 7 h. After distilling off the solvent, 1 M KOH (20 mL) was added, and the mixture was extracted with dichloromethane (40 mL). The organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance. The yield of the obtained 1-phenylethylamine was 81%. It was derivatized to 2,2,2-trifluoro-N-(1-phenylethyl)acetamide by the reaction with 1-phenylethylamine and anhydrous trifluoroacetic acid, and its optical purity was measured by GC analysis to be 12% ee.

Reaction Example 19

Synthesis of DL-1-phenylethylamine

In a 20-mL Schlenk, ammonium formate (MW: 63.06) (946 mg, 15.0 mmol) was charged, and replaced with argon gas. Dehydrated methanol (5 mL), acetophenone (MW: 120.15) (582 µL, 5.0 mmol), acetic acid (286 µL, 5.0 mmol), and catalyst 3 (MW: 624.22) (6.24 mg, 0.01 mmol, S/C=500) were added thereto, and the mixture was stirred with heating at 60° C. for 7 h. After distilling off the solvent, 1 M KOH (20 mL) was added, and the mixture was extracted with dichloromethane (40 mL). The organic layer was dried over sodium sulfate, filtered, and diluted in a 50-mL measuring flask. Five mL of the solution was taken, the solvent was distilled off, and quantification by H-NMR was carried out using coumarin as the internal standard substance. The yield of the obtained DL-1-phenylethylamine was 92%.

Reaction Example 20

Synthesis of DL-1-phenylethylamine

Except for using catalyst 4 (MW: 562.15) (5.62 mg, 0.01 mmol, S/C=500) as the catalyst, reaction was carried out under the same conditions as Reaction Example 19; the yield of the desired product was 83%.

Reaction Example 21

Synthesis of DL-1-phenylethylamine

Except for using acetic acid (572 µL, 10.0 mmol), reaction was carried out under the same conditions as Reaction Example 20; the yield of the desired product was 90%.

Reaction Example 22

Synthesis of DL-1-phenylethylamine

Except for using catalyst 5 (MW: 638.24) (6.38 mg, 0.01 mmol, S/C=500) as the catalyst, reaction was carried out under the same conditions as Reaction Example 19; the yield of the desired product was 62%.

Reaction Example 23

Synthesis of DL-1-phenylethylamine

Except for using catalyst 6 (MW: 638.24) (6.38 mg, 0.01 mmol, S/C=500) as the catalyst, reaction was carried out under the same conditions as Reaction Example 19; the yield of the desired product was 58%.

Reaction Example 24

Synthesis of DL-1-phenylethylamine

Except for using catalyst 7 (MW: 472.83) (4.73 mg, 0.01 mmol, S/C=500) as the catalyst, reaction was carried out under the same conditions as Reaction Example 19; the yield of the desired product was 50%.

Reaction Example 25

Synthesis of cyclohexylbenzylamine

Under an inert gas atmosphere, dehydrated ethyl acetate (5 mL), cyclohexanone (MW: 98.14) (518 µL, 5.0 mmol), and benzylamine (MW: 107.15) (627 µL, 5.75 mmol) were added in a 20-mL Schlenk and cooled with ice. Formic acid (MW: 46.03) (566 µL, 15.0 mmol) was added and stirred for about 5 min, then the ice bath was removed, catalyst 3 (MW: 624.22) (3.12 mg, 0.005 mmol, S/C=1000) was added, and the mixture was stirred at 40° C. for 18 h. After distilling off the solvent, 1 M KOH (15 mL) was added, and the mixture was extracted with dichloromethane (40 mL). The organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance. The yield of the obtained cyclohexylbenzylamine was 100%.

Reaction Example 26

Synthesis of cyclohexylbenzylamine

Except for using catalyst 4 (MW: 562.15) (2.81 mg, 0.005 mmol, S/C=1000) as the catalyst, reaction was carried out under the same conditions as Reaction Example 25; the yield of the desired product was 100%.

Reaction Example 27

Synthesis of cyclohexylbenzylamine

Except for using catalyst 5 (MW: 638.24) (3.19 mg, 0.005 mmol, S/C=1000) as the catalyst, reaction was carried out under the same conditions as Reaction Example 25; the yield of the desired product was 100%.

Reaction Example 28

Synthesis of cyclohexylbenzylamine

Except for using catalyst 6 (MW: 638.24) (3.19 mg, 0.005 mmol, S/C=1000) as the catalyst, reaction was carried out under the same conditions as Reaction Example 25; the yield of the desired product was 100%.

Reaction Example 29

Synthesis of cyclohexylbenzylamine

Except for using catalyst 7 (MW: 472.83) (2.36 mg, 0.005 mmol, S/C=1000) as the catalyst, reaction was carried out under the same conditions as Reaction Example 25; the yield of the desired product was 90%.

Reaction Example 30

Synthesis of N-benzyl-1-indanamine

Under an inert gas atmosphere, dehydrated methanol (5 mL), 1-indanone (MW: 132.16) (661 mg, 5.0 mmol), and benzylamine (MW: 107.15) (600 μL, 5.5 mmol) were added in a 20-mL Schlenk and cooled with ice. Formic acid (MW: 46.03) (566 μL, 15.0 mmol) was added and stirred for about 5 min, then the ice bath was removed, catalyst 4 (MW: 562.15) (5.62 mg, 0.01 mmol, S/C=500) was added, and the mixture was stirred at 40° C. for 18 h. After distilling off the solvent, 1 M KOH (15 mL) was added, and the mixture was extracted with dichloromethane (40 mL). The organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance. The yield of the obtained N-benzyl-1-indanamine was 94%.

Reaction Example 31

Synthesis of 2-[{(S)-1-phenylethyl}amino]propionic acid

A 20-mL Schlenk replaced with argon was cooled to 0° C. in an ice bath, and methanol (2 mL), pyruvic acid (MW: 88.06) (137.6 μL), (S)-1-phenylethylamine (MW: 121.18) (283.6 μL), and formic acid (MW: 46.03) (226.4 μL) were added. (S)-Catalyst 2 (MW: 624.22) (2.50 mg) was added thereto, and the mixture was stirred with heating at 30° C. for 16 h. After 16 h, diethyl ether (20 mL) was added to the reaction mixture and stirred at room temperature for 30 min. The precipitated solid was filtered, washed with diethyl ether (10 mL), and dried under reduced pressure to afford a white solid (283.6 mg, 73% yield). Diastereomer ratio can be determined from the chemical shift in $^1$H-NMR spectrum in heavy water (major: δ1.24 ppm, minor: δ1.33 ppm), and the ratio of major to minor was 92:8 (84% de).

Reaction Example 32

Synthesis of (R)-4-methyl-2-[{(R)-1-phenylethyl}amino]valeric acid

A 20-mL Schlenk replaced with argon was cooled to 0° C. in an ice bath, and methanol (2 mL), 4-methyl-2-oxo-valeric acid (MW: 130.14) (245.5 mL), (R)-1-phenylethylamine (MW: 121.18) (283.6 mL), and formic acid (MW: 46.03) (226.4 mL) were added. (S)-Catalyst 1 (94% ee) (MW: 562.15) (2.25 mg) was added thereto, and the mixture was stirred with heating at 30° C. for 16 h. After 16 h, diethyl ether (20 mL) was added to the reaction mixture and stirred at room temperature for 30 min. The precipitated solid was filtered, washed with diethyl ether (10 mL), and dried under reduced pressure to afford a white solid (333.2 mg, 71% yield). Regarding the diastereomer ratio, generation of a single diastereomer (>99% de) was confirmed from the chemical shift in $^1$H-NMR spectrum in deuterated DMSO. The obtained compound was treated with Pd—C and hydrochloric acid to obtain a leucinate hydrochloride. The optical rotation of this compound was $[\alpha]_D^{20}=-2.9°$ (c=1.15, H$_2$O).

Reaction Example 33

Synthesis of 4-[{(R)-1-phenylethyl}amino]valeric acid

A 20-mL Schlenk replaced with argon was cooled to 0° C. in an ice bath, and methanol (2 mL), levulinic acid (MW: 116.12) (232.2 mg), (R)-1-phenylethylamine (MW: 121.18) (283.6 mL), and formic acid (MW: 46.03) (226.4 mL) were added. (S)-Catalyst 1 (MW: 562.15) (2.25 mg) was added thereto, and the mixture was stirred with heating at 30° C. for 16 h. After 16 h, solvent was removed under reduced pressure, and the resulting mixture was purified by silica gel column chromatography (methylene chloride:methanol=8:1) to afford a white solid (353.0 mg, 80% yield). Diastereomer ratio can be determined from the chemical shift in $^1$H-NMR spectrum in deuterated chloroform (major: δ1.18 ppm, minor: δ1.26 ppm), and the ratio of major to minor was 83:17 (66% de).

Reaction Example 34

Synthesis of methyl 2-[{(R)-1-phenylethyl}amino]propionate

A 20-mL Schlenk replaced with argon was cooled to 0° C. in an ice bath, and methanol (2 mL), methyl pyruvate (MW: 102.09) (180.7 μL), (R)-1-phenylethylamine (MW: 121.18) (283.6 μL), and formic acid (MW: 46.03) (226.4 μL) were added thereto. (S)-Catalyst 1 (94% ee) (MW: 562.15) (2.25 mg) was added, and the mixture was stirred with heating at 30° C. for 16 h. After 16 h, saturated aqueous sodium bicarbonate (10 mL) was added, and the mixture was extracted with diethyl ether (30 mL). The organic layer was dried over sodium sulfate, filtered, and the solvent was distilled off. The obtained crude product was purified by silica gel column chromatography (hexane:ethyl acetate=6:1) to afford a colorless transparent liquid (202.2 mg, 49% yield). Diastereomer ratio can be determined from the chemical shift in 1H-NMR spectrum in deuterated chloroform (major: δ1.22 ppm, minor: δ1.28 ppm), and the ratio of major to minor was 92:8 (84% de).

Reaction Example 35

Synthesis of methyl 2-(benzylamino)propionate

A 20-mL Schlenk replaced with argon was cooled to 0° C. in an ice bath, and methanol (2 mL), methyl pyruvate (MW: 102.09) (180.7 mL), benzylamine (MW: 107.15) (240.5 mL), and formic acid (MW: 46.03) (226.4 mL) were added. (S)-Catalyst 2 (MW: 624.22) (2.50 mg) was added thereto, and the mixture was stirred with heating at 30° C. for 16 h. After 16 h, saturated aqueous sodium bicarbonate (10 mL) was added, and the mixture was extracted with ethyl acetate (30 mL). The organic layer was dried over sodium sulfate, filtered, and the solvent was distilled off. The obtained crude product was purified by silica gel column chromatography (hexane:ethyl acetate=6:1) to afford a colorless transparent liquid (231.7 mg, 60% yield). HPLC analysis was performed, and the optical purity determined using CHIRAL- CEL OD-H (0.46 cm×25 cm) (Daicel Chemical Industries Ltd., eluent; n-hexane:2-propanol=90:10) was 44.3% ee.

Reaction Example 36

Synthesis of 2-[{(R)-1-phenylethyl}amino]-1-propanol

A 20-mL Schlenk replaced with argon was cooled to 0° C. in an ice bath, and methanol (2 mL), hydroxyacetone (MW: 74.08) (137.2 mL), (R)-1-phenylethylamine (MW: 121.18) (283.6 mL), and formic acid (MW: 46.03) (226.4 mL) were added. (S)-Catalyst 1 (MW: 562.15) (2.25 mg) was added thereto, and the mixture was stirred with heating at 30° C. for 16 h. After 16 h, $^1$H-NMR spectrum was measured to confirm the generation of desired product with a conversion rate of 100%. Diastereomer ratio can be determined from the chemical shift in $^1$H-NMR spectrum in deuterated chloroform (major: δ1.15 ppm, minor: δ1.23 ppm), and the ratio of major to minor was 91:9 (82% de).

Reaction Example 37

Synthesis of 2-[{(R)-1-phenylethyl}amino]-1-phthalimidyl-propane

A 20-mL Schlenk replaced with argon was cooled to 0° C. in an ice bath, and methanol (5 mL), methylene chloride (5 mL), phthalsuccinimidyl acetone 2 (MW: 203.19) (406.4 mg), (R)-1-phenylethylamine (MW: 121.18) (283.6 mL), and formic acid (MW: 46.03) (226.4 mL) were added. (S)-Catalyst 1 (MW: 562.15) (5.65 mg) was added thereto, and the mixture was stirred with heating at 30° C. for 16 h. After 16 h, $^1$H-NMR spectrum was measured to confirm the generation of desired product with a conversion rate of 63%. Regarding the diastereomer ratio, generation of a single diastereomer (>99% de) was confirmed in H-NMR spectrum in deuterated chloroform.

Reaction Example 38

Synthesis of (R)-1-(2-methoxyphenyl)-N—((R)-1-phenylethyl)propan-2-amine

In a 20-mL Schlenk, (S)-catalyst 9 (MW: 526.09) (2.63 mg, 0.005 mmol, S/C=500) was charged, then dried under reduced pressure and replaced with argon gas. Methanol (1 mL), 1-(2-methoxyphenyl)propan-2-one (MW: 164.20) (153 μL, 1.0 mmol), (R)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 18 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (78% yield). The resulting compound was deprotected with Pd—C and acetylated, and the optical purity of the obtained acetyl amide compound was measured to be 85% ee.

Reaction Example 39

Synthesis of (R)-1-(2-methoxyphenyl)-N—((R)-1-phenylethyl)propan-2-amine

In a 20-mL Schlenk, (S)-catalyst 10 (MW: 603.18) (3.02 mg, 0.005 mmol, S/C=500) was charged, then dried under reduced pressure and replaced with argon gas. Methanol (1 mL), 1-(2-methoxyphenyl)propan-2-one (MW: 164.20) (153 μL, 1.0 mmol), (R)-1-phenylethylamine (MW: 121.18) (140 μL, 1.1 mmol), and formic acid (MW: 46.03) (113 μL, 3.0 mmol) were added thereto, and the mixture was stirred with heating at 40° C. for 18 h. The solvent was concentrated under reduced pressure, 1 M KOH (10 mL) was added, and the mixture was extracted with dichloromethane (40 mL), then the organic layer was dried over sodium sulfate, filtered, and diluted in a 50-mL measuring flask. Five mL of the solution was taken, the solvent was distilled off, and quantification by $^1$H-NMR was carried out using coumarin as the internal standard substance (84% yield). The resulting compound was deprotected with Pd—C and acetylated, and the optical purity of the obtained acetyl amide compound was measured to be 83% ee.

Reaction Example 40

Synthesis of cyclohexylbenzylamine

Except for using (S)-catalyst 11 (MW: 674.25) (16.9 mg, 0.025 mmol, S/C=200) as the catalyst, reaction was carried out under the same conditions as Reaction Example 25; the yield of the desired product was 98%.

The invention claimed is:
1. An organometallic compound of the following general formula (1):

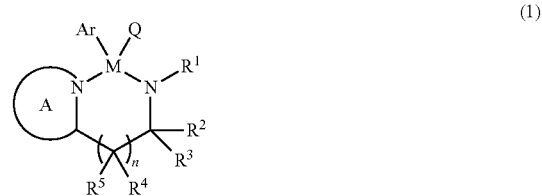

wherein
Ar is a cyclopentadienyl group, in which one or more hydrogen atoms may be substituted by a substituent W, the substituent W is a saturated or unsaturated C1-C20 hydrocarbon group, a 6- to 20-membered aryl group in which a carbon atom may be replaced by a heteroatom, a 3- to 20-membered heterocyclyl group, a C1-C20 alkoxy group, —C(=O)—R$^a$, —C(=O)—OR$^a$, a hydroxyl group, —NR$^a$R$^b$, —C(=O)—NR$^a$R$^b$, a nitro group, a cyano group, —PR$^a$R$^b$, a C1-C20 sulfenyl group, a sulfo group, a mercapto group, —SiR$^a$R$^b$R$^c$, a halogen group or —S(=O)$_2$—R$^a$,
Q is a hydride group or an anionic group,
M is rhodium or iridium,
R$^1$ is an electron withdrawing group,
R$^2$, R$^3$, R$^4$ and R$^5$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a C1-C20 alkoxy group, —C(=O)—OR$^a$, a C1-C20 fluoroalkyl group, —C(=O)—R$^a$, —S(=O), —R, a hydroxyl group, —NR$^a$R$^b$, —(=O)—NR$^a$R$^b$, a C1-C20 sulfenyl group, or —SiR$^a$R$^b$R$^c$, wherein one or more hydrogen atoms of these groups may be substituted by the substituent W, $R^a$, $R^b$ and $R^c$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom, $R^2$ and $R^3$ and/or $R^4$ and $R^5$ may be bonded to each other to form a ring, one of $R^2$ and $R^3$, and one of $R^4$ or $R^5$ may be bonded to each other to form a ring, $R^1$ and $R^2$, or $R^1$ and $R^3$ may be bonded to each other to form a ring, the carbon atom to which $R^2$ and $R^3$ are bonded, and/or the carbon atom to which $R^4$ and $R^5$ are bonded is/are asymmetric carbon atoms, n is 0 or 1, and A is a monocyclic or polycyclic aromatic ring comprising one or more heteroatoms selected from the group consisting of nitrogen, oxygen, and sulfur, provided the ring contains at least one nitrogen atom, wherein one or more hydrogen atoms may be substituted by a substituent W.

2. The organometallic compound according to claim 1, wherein the electron-withdrawing group is —S(=O)$_2$—$R^a$, a 6- to 20-membered aryl group in which a carbon atom may be replaced by a heteroatom, —C(=O)—O$R^a$, —C(=O)—$R^a$, —C(=O)—N$R^a R^b$, —C(=S)—N$R^a R^b$, a C1-C20 sulfenyl group or a perfluoroalkyl group, in which one or more hydrogen atoms of these groups may be substituted by a substituent W, wherein $R^a$ and $R^b$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom.

3. The organometallic compound according to claim 2, wherein the electron-withdrawing group is —S(=O)$_2$—$R^a$, —C(=O)—$R^a$, or —C(=O)—N$R^a R^b$, in which one or more hydrogen atoms of these groups may be substituted by a substituent W.

4. The organometallic compound according to claim 1, characterized in that n is 0.

5. The organometallic compound according to claim 1, wherein A is an aromatic ring having only one nitrogen atom as the ring member heteroatom.

6. The organometallic compound according to claim 1, wherein A is an aromatic ring comprising one or more heteroatoms selected from the group consisting of nitrogen atom, oxygen atom and sulfur atom, in addition to one nitrogen atom.

7. The organometallic compound according to claim 1, wherein the organometallic complex of general formula (1) is an optically active substance.

8. A catalyst used for a reducing reaction or hydrogenation reaction of one or more kinds selected from the group consisting of imine, iminium cation and enamine, or for a reducing reaction or a hydrogenation reaction of one or more kinds selected from the group consisting of imine, iminium cation and enamine that are generated in a system of mixing a carbonyl compound and an amine compound, wherein the catalyst comprises at least one organometallic compound according to claim 1.

9. A method for producing an amine compound, characterized in that the amine compound is produced, under the presence of the organometallic compound according to claim 1, using a hydrogen-donating organic compound or inorganic compound or hydrogen as the hydrogen source, by the reduction or hydrogenation of one or more compounds selected from the group consisting of a compound of general formula (2):

(2)

wherein $R^6$ and $R^7$ are, independently of one another, a hydrogen atom, a hydrocarbyl group, an aryl group in which a carbon atom may be replaced by a heteroatom, a 6- to 20-membered alkylaryl group in which a carbon atom of the aryl may be replaced by a heteroatom, a 6- to 20-membered aralkyl group in which a carbon atom of the aryl may be replaced by a heteroatom, a heterocyclyl group, a carboxyl group, an ester group or an acyl group, wherein one or more hydrogen atoms of these groups may be substituted by a substituent W, $R^8$ is a hydrogen atom, a hydroxyl group, a hydrocarbyl group, an aryl group in which a carbon atom may be replaced by a heteroatom, a 6- to 20-membered alkylaryl group in which a carbon atom of the aryl may be replaced by a heteroatom, a 6- to 20-membered aralkyl group in which a carbon atom of the aryl may be replaced by a heteroatom, a heterocyclyl group, a sulfonyl group in which a carbon atom may be replaced by a heteroatom, an alkoxy group, an acyl group, an ester group, a carboxyl group, a phosphinyl group, a sulfinyl group or a silyl group, wherein one or more hydrogen atoms of these groups may be substituted by a substituent W, $R^6$ and $R^7$, or $R^6$ and $R^8$ may be bonded to each other to form a ring, the substituent W is a saturated or unsaturated C1-C20 hydrocarbon group, a 6- to 20-membered aryl group in which a carbon atom may be replaced by a heteroatom, a 3- to 20-membered heterocyclyl group, a C1-C20 alkoxy group, —C(=O)—$R^a$, —C(=O)—O$R^a$, a hydroxyl group, —N$R^a R^b$, —C(=O)—N$R^a R^b$, a nitro group, a cyano group, —P$R^a R^b$, a C1-C20 sulfenyl group, a sulfo group, a mercapto group, —Si$R^a R^b R^c$, a halogen group or —S(=O)$_2$—$R^a$, and $R^a$, $R^b$ and $R^c$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom;

a cation of general formula (3):

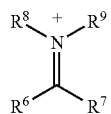

(3)

wherein
R$^6$ and R$^7$ represent the same meanings as defined above,
R$^8$ and R$^9$ are, independently of one another, a hydrogen atom, a hydroxyl group, a hydrocarbyl group, an aryl group in which a carbon atom may be replaced by a heteroatom, a 6- to 20-membered alkylaryl group in which a carbon atom of the aryl may be replaced by a heteroatom, a 6- to 20-membered aralkyl group in which a carbon atom of the aryl may be replaced by a heteroatom, a heterocyclyl group, a sulfonyl group in which a carbon atom may be replaced by a heteroatom, an alkoxy group, an acyl group, an ester group, a carboxyl group, a phosphinyl group, a sulfinyl group or a silyl group, wherein one or more hydrogen atoms of these groups may be substituted by a substituent W,
one or more selected from R$^6$ and R$^7$, R$^6$ and R$^8$, R$^7$ and R$^9$, and R$^8$ and R$^9$, may be bonded to each other to form a ring,
the substituent W is a saturated or unsaturated C1-C20 hydrocarbon group, a 6- to 20-membered aryl group in which a carbon atom may be replaced by a heteroatom, a 3- to 20-membered heterocyclyl group, a C1-C20 alkoxy group, —C(=O)—R$^a$, —C(=O)—OR$^a$, a hydroxyl group, —NR$^a$R$^b$, —C(=O)—NR$^a$R$^b$, a nitro group, a cyano group, —PR$^a$R$^b$, a C1-C20 sulfenyl group, a sulfo group, a mercapto group, —SiR$^a$R$^b$R$^c$, a halogen group or —S(=O)$_2$—R$^a$, and
R$^a$, R$^b$ and R$^c$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom; and a compound of general formula (4):

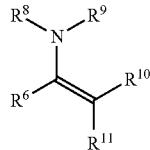

(4)

wherein
R$^6$, R$^8$, and R$^9$ have the same meanings as defined above,
R$^{10}$ and R$^{11}$ are, independently of one another, a hydrogen atom, a hydrocarbyl group, an aryl group in which a carbon atom may be replaced by a heteroatom, a heterocyclyl group, a carboxyl group, an ester group, or an acyl group, wherein one or more hydrogen atoms of these groups may be substituted by a substituent W,
one or more selected from R$^6$ and R$^8$, R$^6$ and R$^{11}$, R$^8$ and R$^9$, R$^9$ and R$^{10}$, and R$^{10}$ and R$^{11}$, may be bonded to each other to form a ring,
the substituent W is a saturated or unsaturated C1-C20 hydrocarbon group, a 6- to 20-membered aryl group in which a carbon atom may be replaced by a heteroatom, a 3- to 20-membered heterocyclyl group, a C1-C20 alkoxy group, —C(=O)—R$^a$, —C(=O)—OR$^a$, a hydroxyl group, —NR$^a$R$^b$, —C(=O)—NR$^a$R$^b$, a nitro group, a cyano group, —PR$^a$R$^b$, a C1-C20 sulfenyl group, a sulfo group, a mercapto group, —SiR$^a$R$^b$R$^c$, a halogen group or —S(=O)$_2$—R$^a$, and
R$^a$, R$^b$ and R$^c$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom;
or
one or more compounds selected from the group consisting of a compound of general formula (2), a cation of general formula (3), and a compound of general formula (4), which are generated by mixing a carbonyl compound and an amine compound in a system.

10. The method for producing an amine compound according to claim 9, wherein the carbonyl compound is a compound of general formula (7):

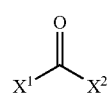

(7)

wherein
X$^1$ and X$^2$ are, independently of one another, a hydrogen atom, a hydroxyl group, a hydrocarbyl group, an aryl group in which a carbon atom may be replaced by a heteroatom, an alkylaryl group in which a carbon atom of the aryl may be replaced by a heteroatom, an aralkyl group in which a carbon atom of the aryl may be replaced by a heteroatom, a heterocyclyl group, a carboxyl group, an ester group, or an acyl group, wherein one or more hydrogen atoms of these groups may be substituted by a substituent W,
the substituent W is a saturated or unsaturated C1-C20 hydrocarbon group, a 6- to 20-membered aryl group in which a carbon atom may be replaced by a heteroatom, a 3- to 20-membered heterocyclyl group, a C1-C20 alkoxy group, —C(=O)—R$^a$, —C(=O)—OR$^a$, a hydroxyl group, —NR$^a$R$^b$, —C(=O)—NR$^a$R$^b$, a nitro group, a cyano group, —PR$^a$R$^b$, a C1-C20 sulfenyl group, a sulfo group, a mercapto group, —SiR$^a$R$^b$R$^c$, a halogen group or —S(=O)$_2$—R$^a$, R$^a$, R$^b$ and R$^c$ are, independently of one another, a hydrogen atom, a saturated or unsaturated C1-C20 alkyl group, a saturated or unsaturated C3-C20 cycloalkyl group, a 6- to 20-membered aryl group in which a carbon atom may be replaced by a heteroatom, a 3- to 20-membered heterocyclyl group, a 6- to 20-membered aralkyl group in which a carbon atom of the aryl may be replaced by a heteroatom, a 6- to 20-membered alkylaryl group in which a carbon atom of the aryl may be replaced by a heteroatom,
X$^1$ and X$^2$ may be bonded to each other to form a ring; and
the amine compound to be mixed with the carbonyl compound in a system is an amine of general formula (8) or a salt thereof:

NHY$^1$Y$^2$ (8)

wherein
Y$^1$ and Y$^2$ are, independently of one another, a hydrogen atom, a hydroxyl group, a hydrocarbyl group, an aryl group in which a carbon atom may be replaced by a heteroatom, a 6- to 20-membered aralkyl group in which a carbon atom of the aryl may be replaced by a heteroatom, a 6- to 20-membered alkylaryl group in which a carbon atom of the aryl may be replaced by a heteroatom, a heterocyclyl group, a sulfonyl group in which a carbon atom may be replaced by a heteroatom, an alkoxy group, an acyl group, an ester group, a carboxyl group, a phosphinyl group, a sulfinyl group or a silyl group, wherein one or more hydrogen atoms of these groups may be substituted by the substituent W, $Y^1$ and $Y^2$ may be bonded to each other to form a ring.

11. The method for producing an amine compound according to claim 9, characterized in that one or more compounds selected from the group consisting of a compound of general formula (2), a cation of general formula (3) and a compound of general formula (4) are optically active compounds, or one or more compounds selected from the group consisting of a compound of general formula (2), a cation of general formula (3) and a compound of general formula (4) are optically active compounds generated by the reaction of an optically active amine and a carbonyl compound.

12. The method for producing an amine compound according to claim 9, wherein the hydrogen-donating organic or inorganic compound is formic acid or formate.

13. The organometallic compound according to claim 1, selected from the group consisting of:

(S)-Complex 1

(S)-Complex 2

Complex 3

Complex 4

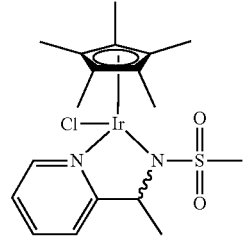

Complex 5

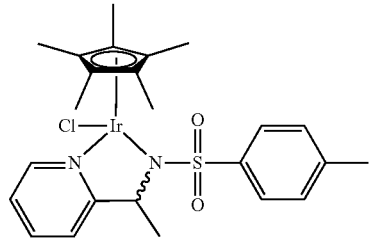

Complex 6

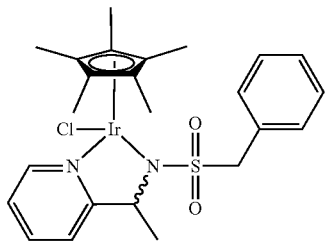

Complex 7

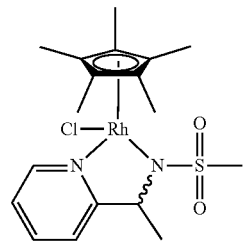

Complex 8

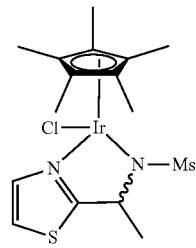

(S)-Complex 9

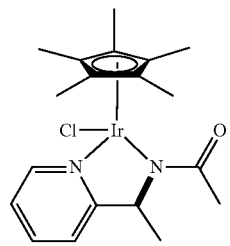

(S)-Complex 10
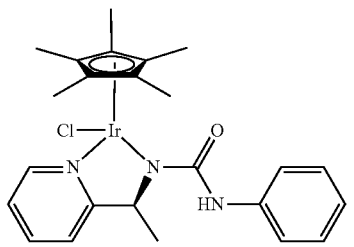
and
Complex 11
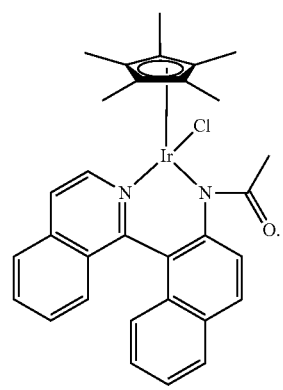
* * * * *